United States Patent
Suzuki et al.

(10) Patent No.: US 7,486,759 B2
(45) Date of Patent: Feb. 3, 2009

(54) X-RAY COMPUTER TOMOGRAPHY APPARATUS

(75) Inventors: Masakazu Suzuki, Kyoto (JP); Takahiro Yoshimura, Kyoto (JP); Makoto Honjo, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 11/974,049

(22) Filed: Oct. 11, 2007

(65) Prior Publication Data
US 2008/0137802 A1 Jun. 12, 2008

(30) Foreign Application Priority Data
Oct. 12, 2006 (JP) .............................. 2006-278615

(51) Int. Cl.
A61B 6/00 (2006.01)
A61B 6/14 (2006.01)
(52) U.S. Cl. ................................ 378/4; 378/38; 378/39
(58) Field of Classification Search ..................... 378/4, 378/15, 19, 38, 39, 98.8, 193, 197
See application file for complete search history.

(56) References Cited

U.S. PATENT DOCUMENTS 6,493,415 B1 * 12/2002 Arai et al. ...................... 378/4
7,197,109 B2 * 3/2007 Rotondo et al. ............... 378/39
7,269,242 B2 * 9/2007 Tanaka et al. ................. 378/16
7,315,608 B2 * 1/2008 Sa et al. ........................ 378/38
2003/0235265 A1 * 12/2003 Clinthorne et al. ............. 378/4

FOREIGN PATENT DOCUMENTS

JP 10-225455 8/1998
JP 3540916 1/1999

* cited by examiner

Primary Examiner—Irakli Kiknadze
(74) Attorney, Agent, or Firm—William L. Androlia; H. Henry Koda

(57) ABSTRACT

There is provided a new X-ray imaging apparatus by the use of which X-ray CT and panoramic imaging can be effectively performed. In an X-ray imaging apparatus which rotates an X-ray generating section and an X-ray detecting section around an imaging object arranged between these X-ray generating section and the X-ray detecting section and also detects in the X-ray detecting section X-rays having been radiated from the X-ray generating section and transmitted through the imaging object to form an X-ray image, a panoramic imaging mode in which the X-ray generating section and the X-ray detecting section are driven to form a panoramic image of the imaging object and an offset scan/CT mode in which the X-ray generating section and the X-ray detecting section are driven to form a tomographic image of the imaging object are set, so as to selectively execute these two imaging modes. Consequently, the panoramic imaging mode and the offset scan/CT mode can be arbitrarily selected, thereby allowing formation of an X-ray imaged image that is optimum for treatment.

6 Claims, 17 Drawing Sheets

Fig. 18A
Fig. 18B
Fig. 18C
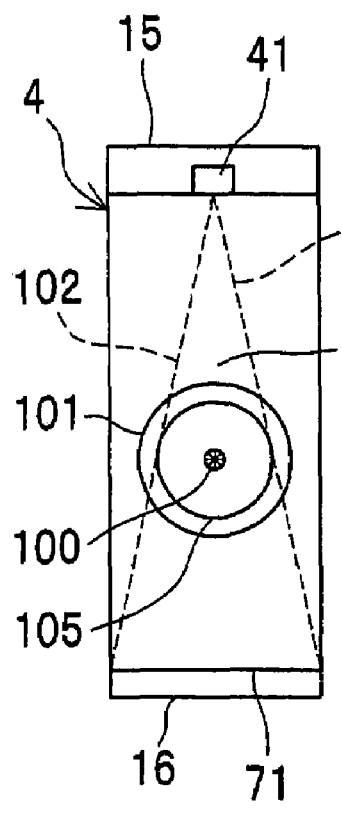
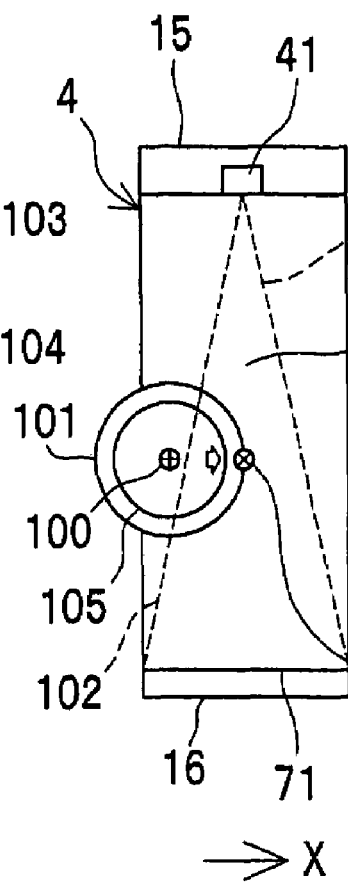
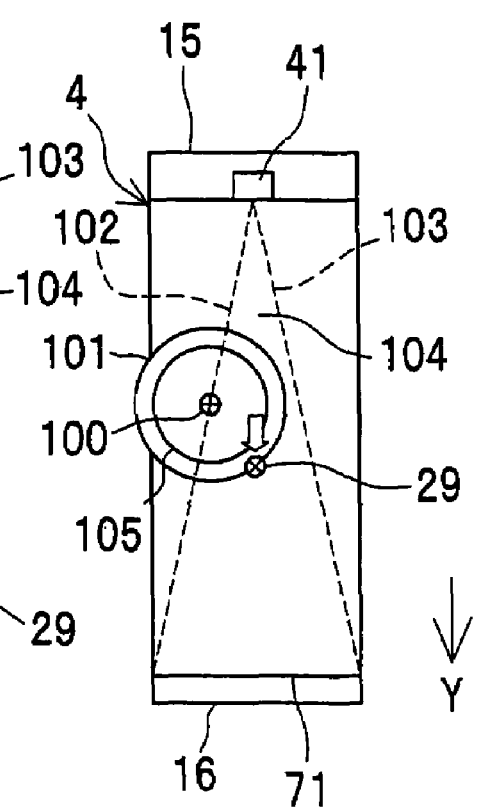

X-RAY COMPUTER TOMOGRAPHY APPARATUS

BACKGROUND OF THE INVENTION

1. Field of the Invention

The present invention relates to an X-ray computer tomography (CT) apparatus for dentistry or a jaw/face region. In particular, the present invention relates to an X-ray CT apparatus capable of performing local X-ray CT on a certain tooth or the like as an region of interest in dentistry or the jaw/face region, and performing panoramic X-ray imaging on a curved cross section of a dental arch, a jaw joint, and the like.

2. Description of the Related Art

The Japanese Patent Publication No. 10-225455 (A) discloses an X-ray CT apparatus for dental diagnosis. This X-ray CT apparatus is one having a local X-ray computer tomography (hereinafter referred to as "CT") along with a panoramic X-ray imaging mode. This X-ray CT apparatus is capable of selecting the X-ray CT mode and the panoramic X-ray imaging mode, and characterized as follows: when the X-ray CT mode is selected, a rotational central axis is fixed onto a central axis of an region of interest, and when the panoramic X-ray imaging mode is selected, a rotational arm having an X-ray generator and an X-ray detector is rotationally moved while the rotational central axis moves along a locus for the panoramic X-ray imaging during imaging.

The Japanese Patent No. 3540916 (B) discloses a three-dimensional X-ray CT scanner, having in a hollow rotating body an X-ray generator and an X-ray detector which are opposed to each other with a horizontal central axis (rotational axis) provided therebetween. In this apparatus, while these X-ray generator and X-ray detector are rotated with respect to an imaging object positioned inside the rotating body, X-rays having been radiated from the X-ray generator and transmitted through the imaging object are detected in the X-ray detector, and using the X-ray image detected in the X-ray detector, a three-dimensional tomographic image can be reconstructed, so that an offset scan/CT method by which a three-dimensional CT image in a larger range than a visual field angle of a two-dimensional X-ray detector is obtained in addition to a so-called normal scan/CT method by which a CT image is obtained by irradiating the whole of the imaging object with X-rays.

This offset scan/CT method has the advantage of being capable of performing X-ray CT in a larger range than the visual field angle of the two-dimensional X-ray detector since part of the region of interest of the imaging object may be irradiated with X-rays at each time point during imaging, as compared with the normal scan/CT method of constantly irradiating the whole of the region of interest of the imaging object with X-rays at each time point during imaging.

SUMMARY OF THE INVENTION

There has been a problem with a conventional X-ray CT apparatus for jaw/face imaging in dentistry and the like in that, since the normal scan/CT method is a dominant method, in the case of performing CT by detecting a range not smaller than a visual field detectable by a two-dimensional X-ray sensor, a large-sized two-dimensional X-ray sensor is required, which causes a cost increase.

In view of the above situation, an object of the present invention is to provide a new X-ray imaging apparatus capable of performing CT on an region of interest such as a jaw/face by an offset scan/CT method using a relatively small two-dimensional X-ray sensor and also capable of performing panoramic X-ray imaging, and to provide a new X-ray imaging apparatus capable of switching the method to a normal scan/CT method in the case of the region of interest being smaller than a visual field angle of the X-ray two-dimensional sensor.

In order to achieve such an object, the present invention is an X-ray CT apparatus, which comprises an X-ray generating section that applies X-rays and an X-ray detecting section in opposing positions, and which rotates said X-ray generating section and X-ray detecting section with an imaging object arranged between said X-ray generating section and X-ray detecting section and also detects X-rays having been radiated from said X-ray generating section and transmitted through said imaging object in said X-ray detecting section to back-project X-ray CT data, so as to form a CT image, wherein said apparatus comprises an imaging mode selecting device for selecting:

a panoramic imaging mode in which, during imaging, a rotational arm having said X-ray generating section and X-ray detecting section is rotationally driven while a rotational central axis of the rotational arm is moved, to form a panoramic image of said imaging object; and an offset scan/CT mode in which a CT image of said imaging object is constructed on the basis of X-ray CT data obtained by rotating the rotational arm around a rotational central axis wherein the rotational arm is set in such a position as a part of a region of interest of said imaging object is constantly irradiated with a cone beam radiated from said X-ray generating section and detected in said X-ray detecting section.

An X-ray imaging apparatus in another aspect of the present invention including the imaging mode selecting means has a normal scan/CT mode in which a CT image of the imaging object is constructed on the basis of X-ray CT data obtained by rotating the rotational central axis of the rotational arm as the center that is provided in such a position as to constantly irradiate an region of interest of the imaging object with a cone beam radiated from the X-ray generating section and detected in the X-ray detecting section.

An X-ray imaging apparatus in another aspect of the present invention including a first slit which forms an X-ray beam, radiated from the X-ray generating section, into narrow strip shape to rotate a narrow beam toward said imaging object in accordance with said panoramic imaging mode;

a second slit which forms an X-ray beam, radiated from the X-ray generating section toward said imaging object, into a cone beam in accordance with at least either one of said offset scan/CT mode and said normal scan/CT mode; and a slit moving device for selectively arranging said first slit and said second slit in said X-ray generating section.

An X-ray imaging apparatus in another aspect of the present invention is provided with a means of moving the first slit or the second slit arranged in the X-ray generating section to a direction orthogonal to the X-ray beam in accordance with a signal from the imaging mode selecting means.

An X-ray imaging apparatus in another aspect of the present invention includes a driving device for moving the rotational central axis of the rotational arm against the rotational arm to set in such a position as to constantly irradiate a part or the whole of a region of interest of said imaging object with said cone beam in accordance with at least one of said offset scan/CT mode and said normal scan/CT mode.

An X-ray imaging apparatus in another aspect of the present invention includes a driving device for moving said rotational central axis in accordance with a rotational angle of the rotational arm that holds said X-ray generating section and said X-ray detecting section.

According to the X-ray imaging apparatus (claim 1) of the present invention, a panoramic imaging mode or an offset scan/CT mode can be arbitrarily selected by the imaging mode selecting means of selecting the panoramic imaging mode or the offset scan/CT mode. It is thereby possible to perform panoramic imaging and offset scan/CT using a costless small two-dimensional X-ray sensor, and as necessary or upon request, it is possible to continuously acquire a panoramic image and an offset scan/CT image which are optimum for treatment. Accordingly, when an approximate position of an region of interest is obtained by panoramic imaging having a large imaging region and an imaging position is then set to perform the offset scan/CT on the region of interest, it is possible to perform CT in a larger range than a conventional range, so as to perform CT in a large range while holding down cost.

According to the X-ray imaging apparatus (claim 2) of the present invention, since the offset scan/CT mode and the normal scan/CT mode are selected as necessary, the convenience in CT increases, and hence with the use of CT, it is possible to acquire a CT image with even higher resolution.

According to the X-ray imaging apparatus (claim 3) of the present invention, a slit corresponding to the panoramic imaging mode or the CT mode is selectively arranged, and it is thereby possible to obtain the optimum X-ray beam required for each imaging mode.

According to the X-ray imaging apparatus (claim 4) of the present invention, the first or the second slit is adjusted to use only an X-ray inclined at a certain angle from the X-ray irradiation central axis, and it is thereby possible to efficiently obtain clear X-ray image data.

According to the X-ray imaging apparatus (claim 5, 6) of the present invention, the driving means is provided which moves the rotational central axis of the central arm in accordance with either the panoramic imaging mode or the CT mode selected by the imaging mode selecting means of selecting either mode, and it is thereby possible to obtain an arbitrary locus of the rotating means that is optimum for imaging.

BRIEF DESCRIPTION OF THE DRAWINGS

FIG. 18 is a pattern view explaining an initial setting process for an enlarged CT mode.

DETAILED DESCRIPTION OF THE PREFERRED EMBODIMENTS

Figure 1:
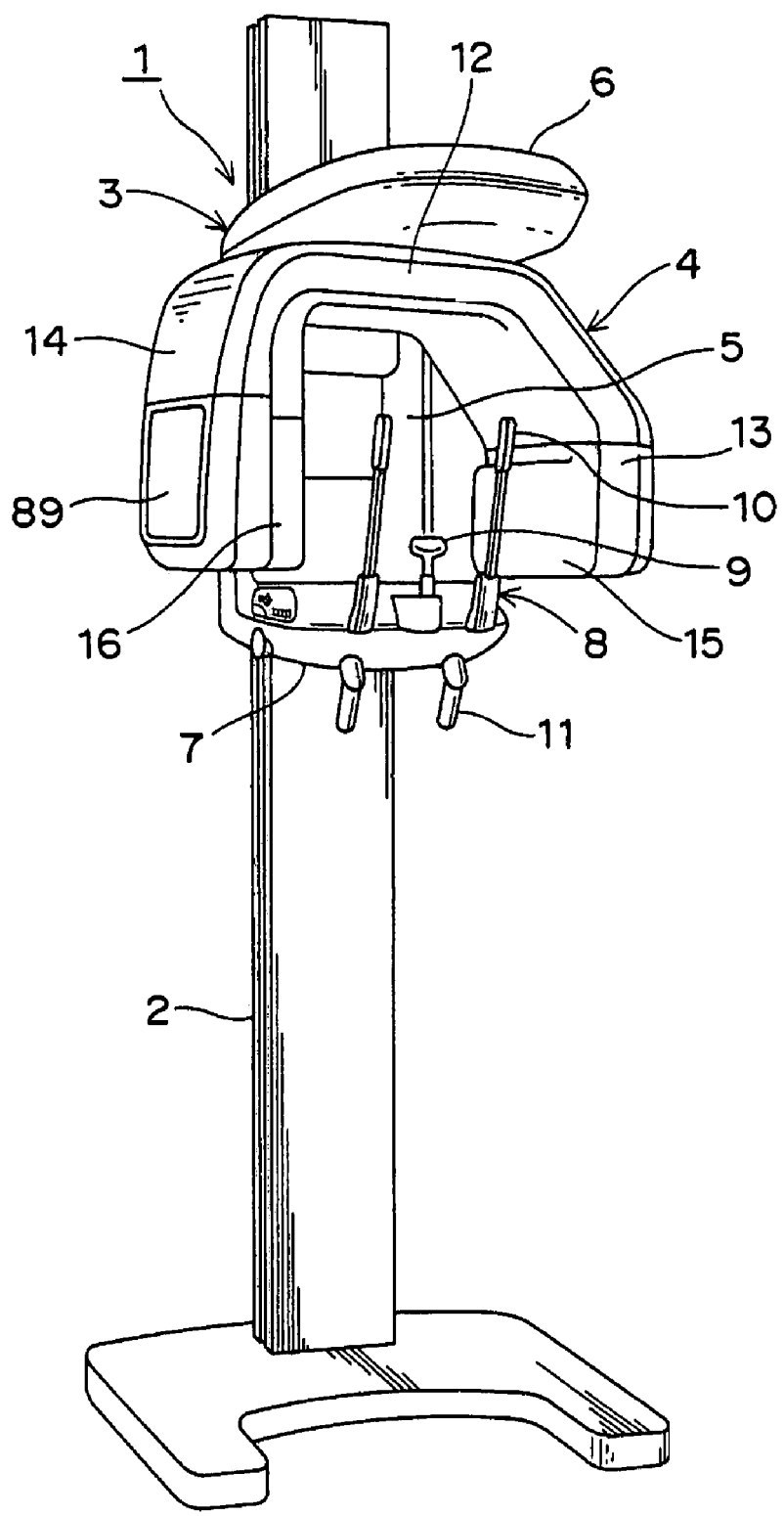
FIG. 1 is a perspective view of an X-ray imaging apparatus of a first example according to the present invention.

With reference to the attached drawings, several embodiments of the X-ray imaging apparatus according to the present invention will be described below. It is to be noted that, although terms that mean a specific direction or a place (e.g. "upper", "lower", "left", "right" and other terms including those terms) are used in the following description, these terms are used for the purpose of facilitating visual understanding of configurations represented in the drawings, and should not be used for defining a technical range of the invention.

FIGS. 1 to 5 show respective appearances of an X-ray CT apparatus according to one embodiment of the present invention. The X-ray CT apparatus is capable of performing three-dimensional computer X-ray tomography (Computer Tomography: hereinafter referred to as "CT") in addition to a variety of imaging which are conventionally widely known in the dentistry field (e.g. panoramic imaging, linear tomography, linear scan imaging, scanogram imaging). It is to be noted that, although the X-ray CT apparatus of the embodiment is an X-ray CT apparatus for dentistry, application of the present invention is not restricted to the X-ray CT apparatus for dentistry, but the present invention is equally applicable to an X-ray CT apparatus for another sort of medical use. For example, although the X-ray CT apparatus shown in the figures is a vertical X-ray imaging apparatus and used with a test object in a standing state, the present invention is also applicable to a so-called lateral X-ray imaging apparatus which is used with a test object held in a horizontally lying state.

As apparent from the figures, an X-ray CT apparatus (hereinafter simply referred to as "imaging apparatus") 1 generally has a vertical column 2 fixed to a floor face; a lifting arm (first frame) 3 liftably provided along the vertical column 2 and a rotational arm (second frame) 4 rotatably coupled to the lifting arm 3 with a vertical rotational central axis (described later with reference to FIGS. 6 to 8) as the center.

Figure 3:
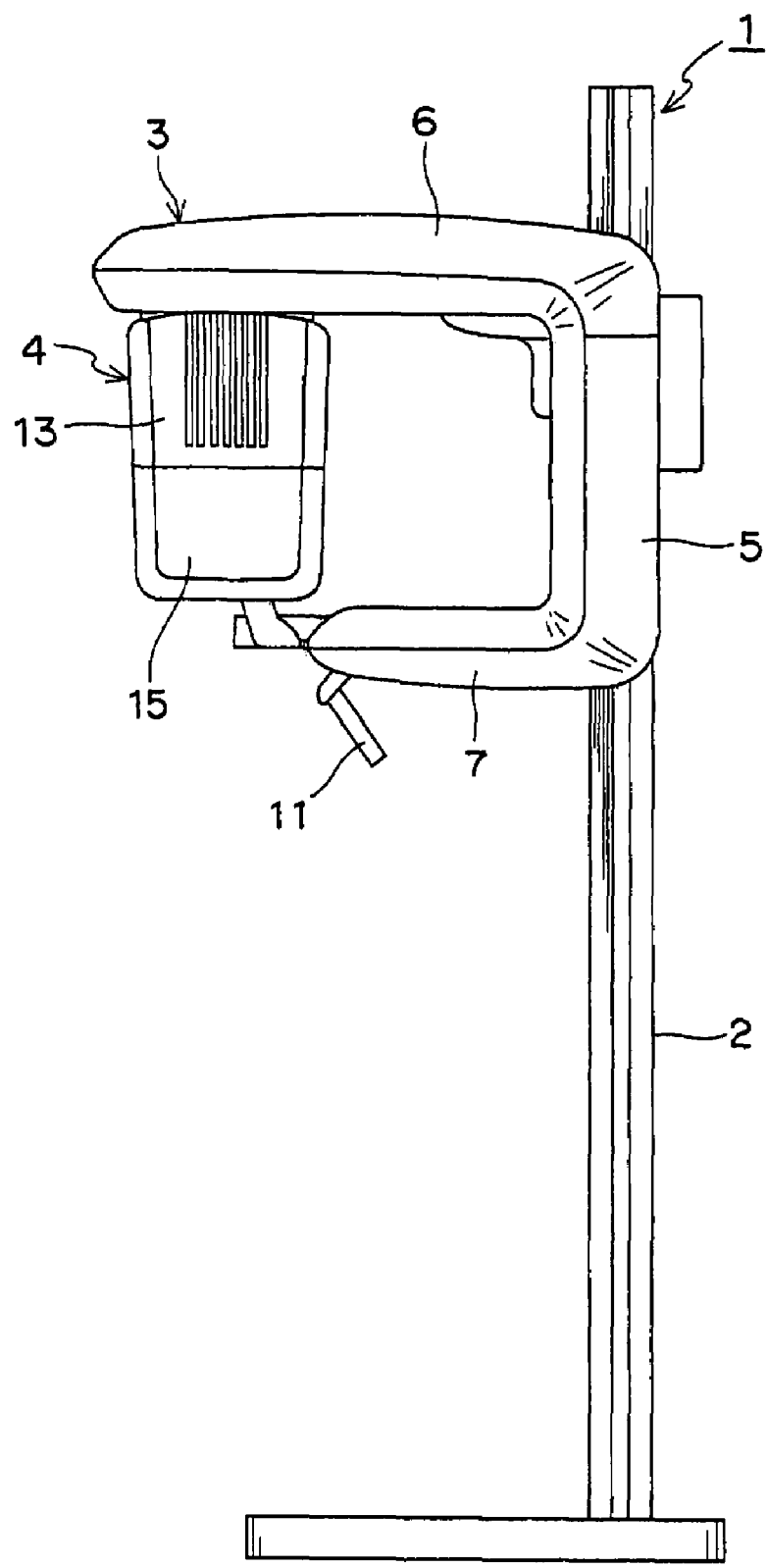
FIG. 3 is a right side view of the X-ray imaging apparatus of the first example according to the present invention.
Figure 4:
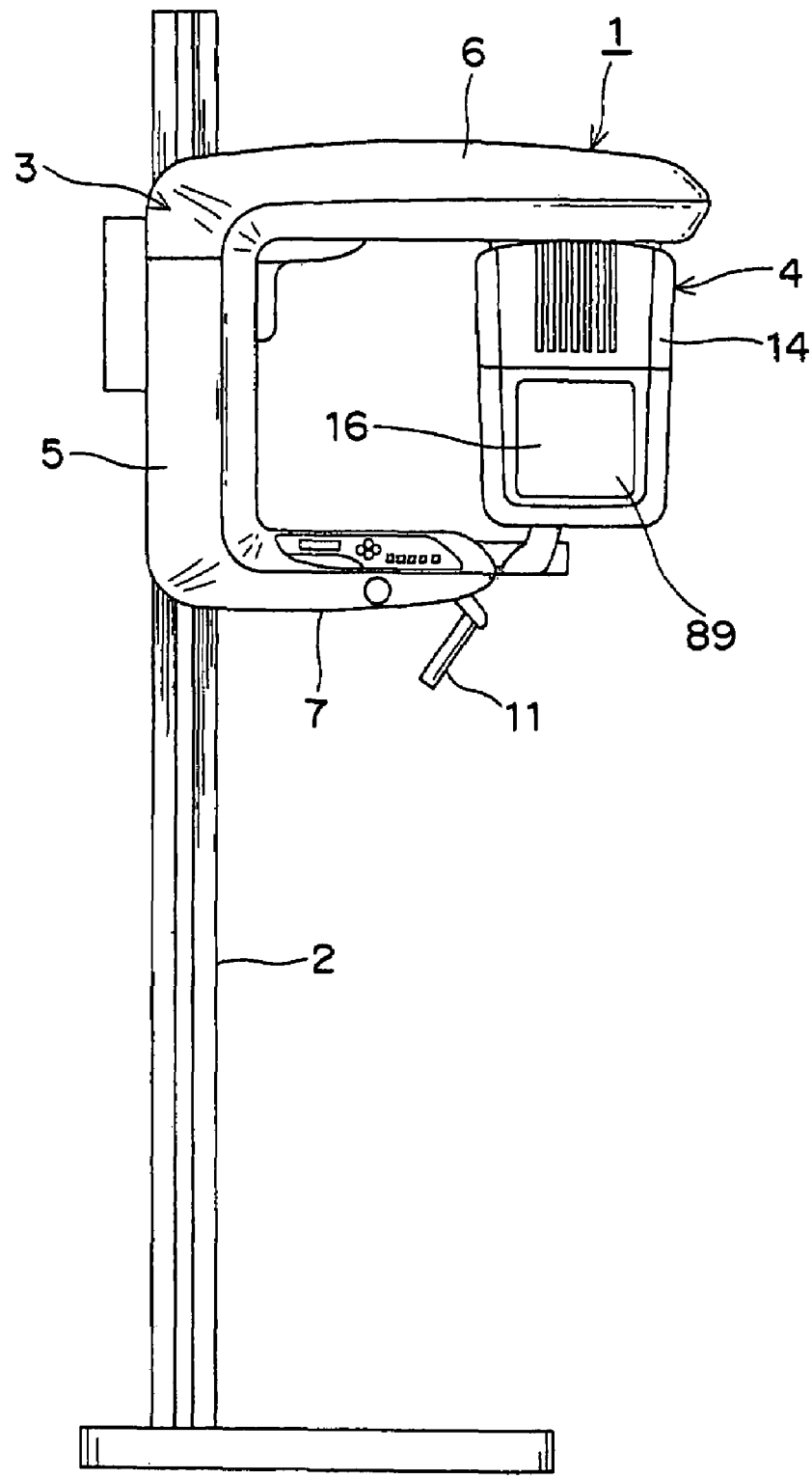
FIG. 4 is a left side view of the X-ray imaging apparatus of the first example according to the present invention.
Figure 5:
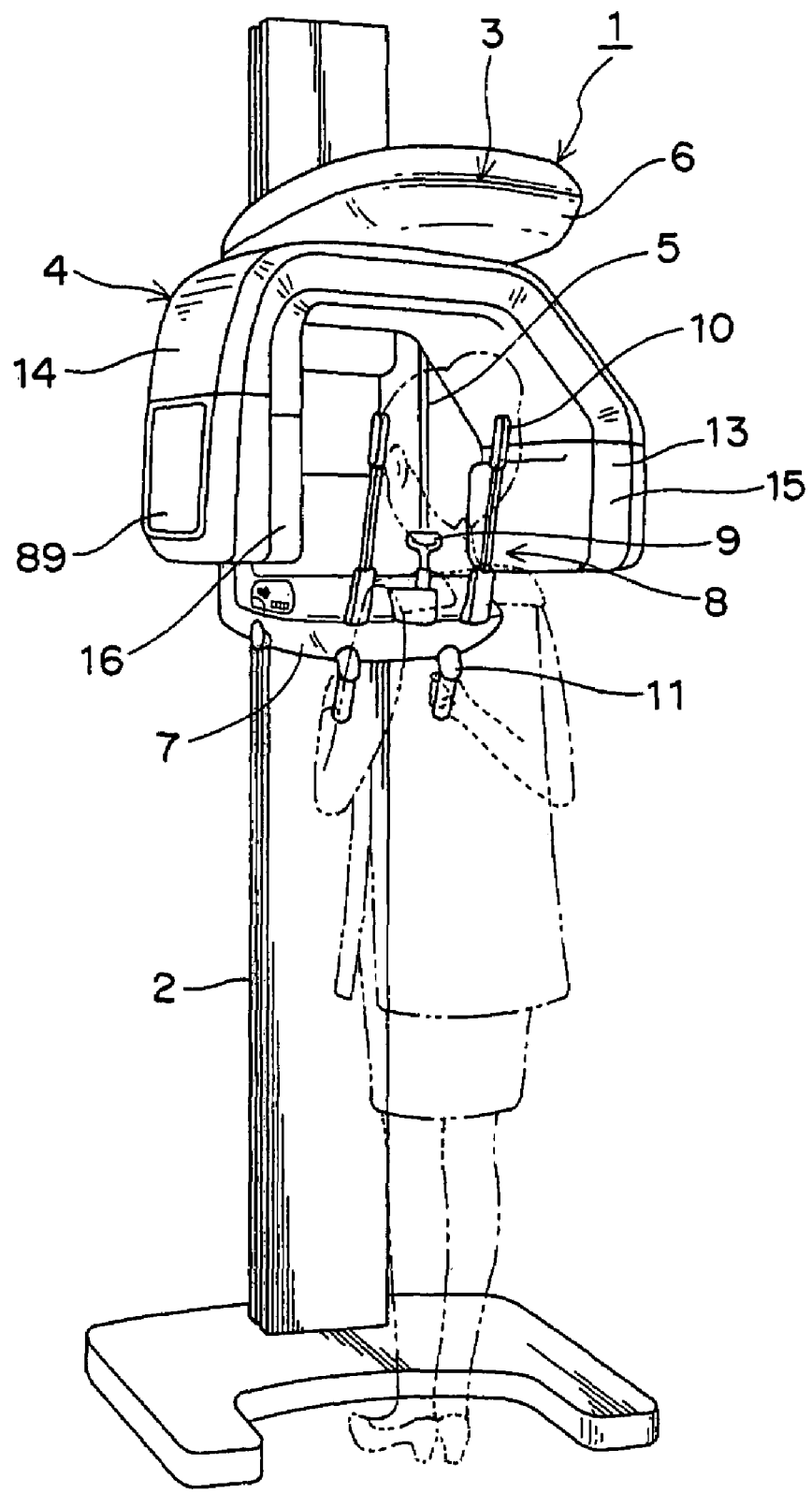
FIG. 5 is a perspective view showing the X-ray imaging apparatus of the first example according to the present invention and a test object positioned therein.

As shown in FIGS. 3 and 4, the lifting arm 3 as a whole has a substantially U shape, and roughly has a vertical arm section 5 liftably coupled to the vertical column 2, and an upper arm section 6 and a lower arm section 7 respectively extending forward (toward the left side of FIG. 3 and the right side of the FIG. 4) from an upper end and a lower end of the vertical arm section 5. As described later, the upper arm section 6 rotatably supports the rotational arm 4 arranged between the upper arm section 6 and the lower arm section 7. As shown in FIG. 5, the lower arm section 7 has thereon a positioning mechanism 8 which positions a head of a person as an imaging object. For example, the positioning mechanism 8 of the X-ray CT apparatus 1 of the embodiment has a chin rest 9 which supports a jaw therefrom, a pair of lateral direction control member 10 which support the head of the test object as the imaging object from the right and left side thereof, and a pair of handles 11 held by the positioned person with his or her both hands so as to be kept stable.

Figure 2:
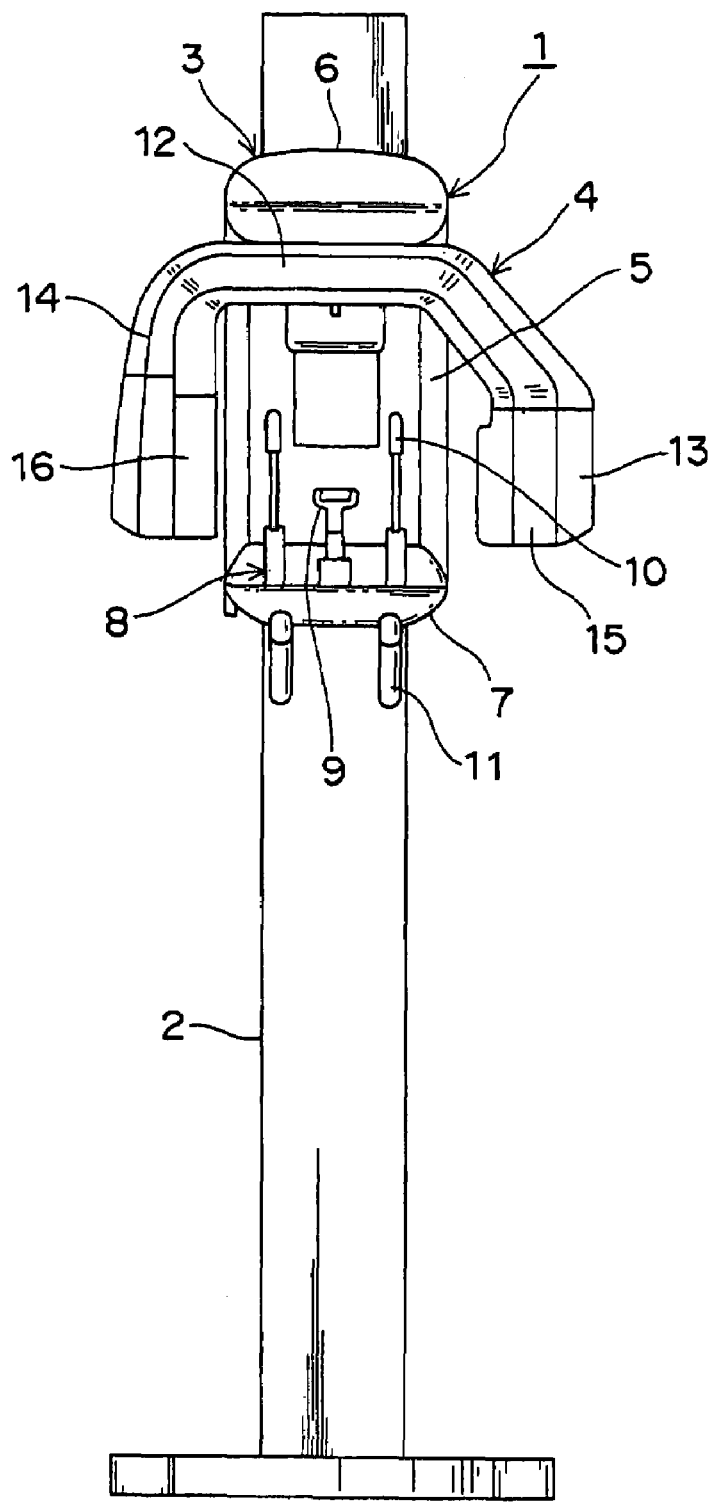
FIG. 2 is a front view of the X-ray imaging apparatus of the first example according to the present invention.

As shown in FIGS. 1 and 2, the rotational arm 4 as a whole has a substantially inverted U shape, and roughly has: a horizontal arm section 12 which is rotatably suspendedly supported by the upper arm section 6 through a later-described coupling mechanism while suspendedly arranged under the upper arm section 6; and first and second suspending section 13 and 14 respectively extending downward from a right and left end of the horizontal arm section 12. The first suspending section 13 shown on a right side of FIG. 2 has an X-ray generating section 15, and the second suspending section 14 shown on a left side of FIG. 2 has an X-ray detecting section 16. The X-ray generating section 15 and the X-ray detecting section 16 are opposed to each other with a prescribed spacing. A horizontal direction in which the X-ray generating section 15 and the X-ray detecting section 16 are opposed to each other is referred to as an "X-direction", a horizontal direction orthogonal thereto is referred to as a "Y-direction", and a height direction is referred to as a "Z-direction".

Figure 6:
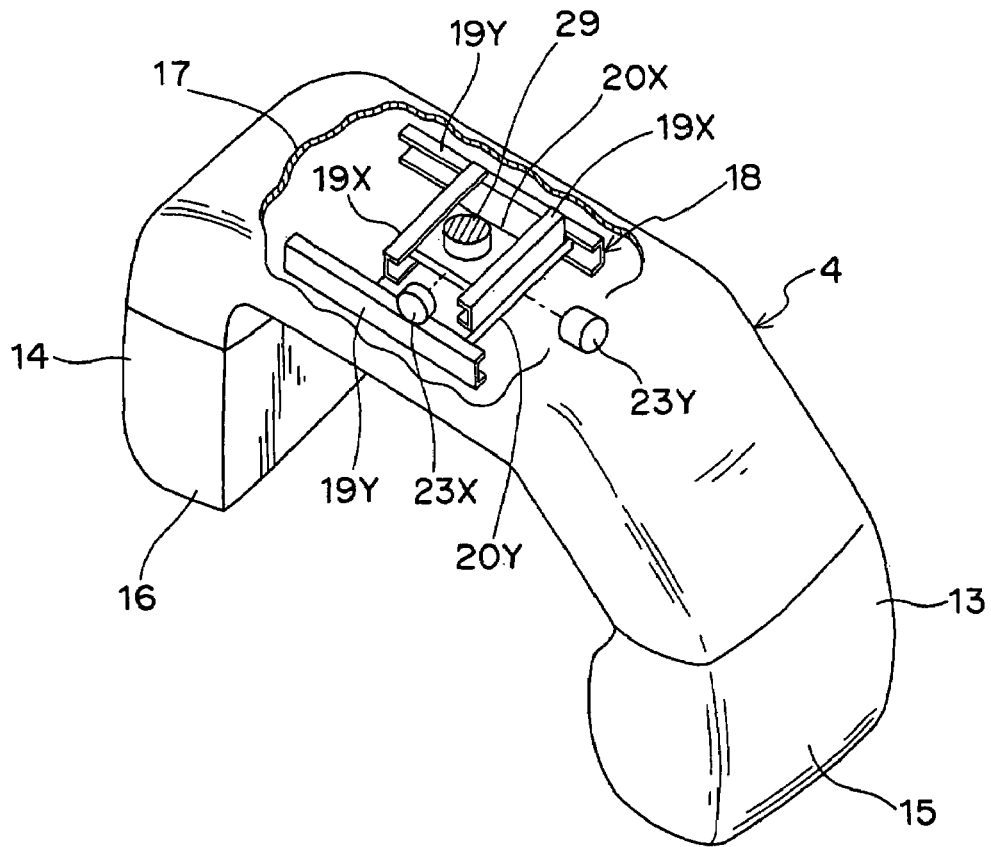
FIG. 6 is a perspective view of a part cutting out from a rotational arm of the X-ray imaging apparatus of the first example shown in FIG. 1.
Figure 7:
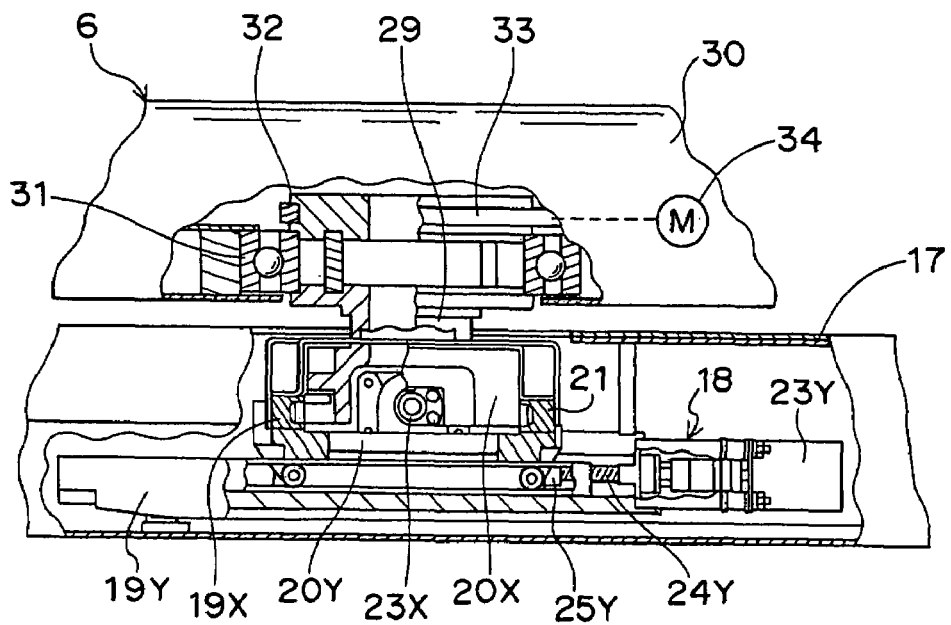
FIG. 7 is a sectional view showing an XY movement mechanism of the rotational arm of the first example.
Figure 8:
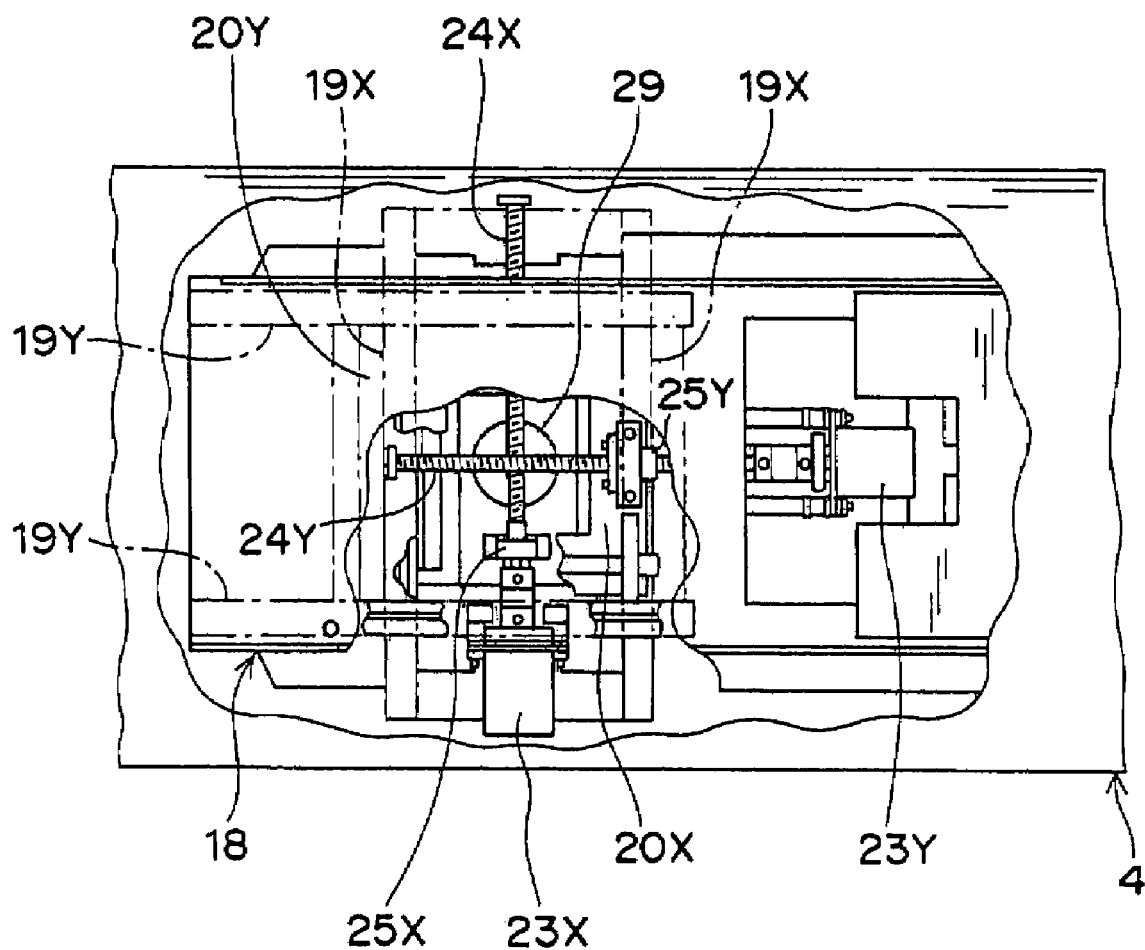
FIG. 8 is a view, seen from the below, of the XY movement mechanism of the rotational arm of the first example.

The coupling mechanism (second coupling means) that couples the lifting arm 3 and the rotational arm 4 is described with reference to FIGS. 6 to 8. The coupling mechanism has an XY movement mechanism (first and second movement mechanisms) 18 housed in a rotational arm housing 17. The XY movement mechanism 18 has a pair of Y-direction guide rails 19Y fixed to the rotational arm housing 17 and extending in the Y-direction, a Y-direction moving frame 20Y capable of reciprocating in the Y-direction along those Y-direction guide rails 19Y, a pair of X-direction guide rails 20X fixed to the Y-direction moving frames 20Y and extending in the X-direction, and an X-direction moving frame 20X capable of reciprocating in the X-direction along those X-direction guide rails 19X. The Y-direction moving frame 20Y is coupled to a Y-direction moving motor 23Y fixed to the rotational arm housing 17 through an appropriate drive transmission mechanism (e.g. mechanism including a screw 24Y drivingly coupled to the motor 23Y and a nut 25Y engaged therein and fixed to the frame 20Y), so that the Y-direction moving frame 20Y moves in the Y-direction on the basis of drive of the Y-direction moving motor 23Y. Similarly, the X-direction moving frame 20X is coupled to the X-direction moving motor 23X fixed to the Y-direction moving frame 20Y through an appropriate drive transmission mechanism (e.g., mechanism including a screw 24X drivingly coupled to the motor 23X and a nut 25X engaged therein and fixed to the X-direction moving frame 20X), so that the X-direction moving frame 20X moves in the X-direction on the basis of drive of the X-direction moving motor 23X. As thus described, in the XY movement mechanism 18, the pair of Y-direction guide rails 19Y, the Y-direction moving frame 20Y, the Y-direction moving motor 23Y, and the drive transmission mechanism therefor (screw 24Y, nut 25Y) constitute the Y-direction movement mechanism, and the pair of X-direction guide rails 19X, the X-direction moving frame 20X, the X-direction moving motor 23X, and the drive transmission mechanism therefor (screw 24X, nut 25X) constitute the X-direction movement mechanism. Therefore, driving the moving motors 23X and 23Y can lead to arbitrary movement of the rotational central axis of the rotational arm.

A rotational central axis 29 in a cylindrical shape or a columnar shape coupling the lifting arm 3 and the rotational arm 4 is fixed to the X-direction moving frame 20X at its upper end and rotatably supported by an axis bearing 31 (first coupling means) built in the rotational arm 4. Further, a belt winding section 32 having a circular shape in its cross section is formed at a lower end of the rotational central axis 29, and a belt 33 is wound around this belt winding section (pulley) 32. The belt 33 is also drivingly coupled to another belt winding section 32 to which a rotational motor 34 built in the rotational arm 4 is drivingly coupled, so that the rotational central axis 29 and the rotational arm 4 fixed thereto are rotated on the basis of drive of the rotational motor 34. These configurations are those having been used basically in the X-ray CT apparatus for dentistry.

Figure 9A:
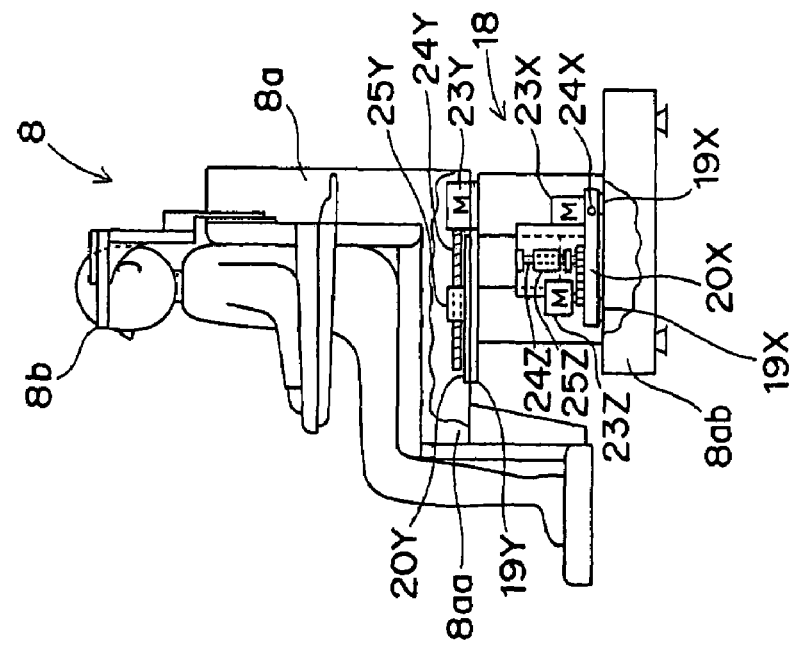
FIG. 9 is a sectional view showing an XY movement mechanism of an imaging object of a second example according to the present invention.
Figure 9B:
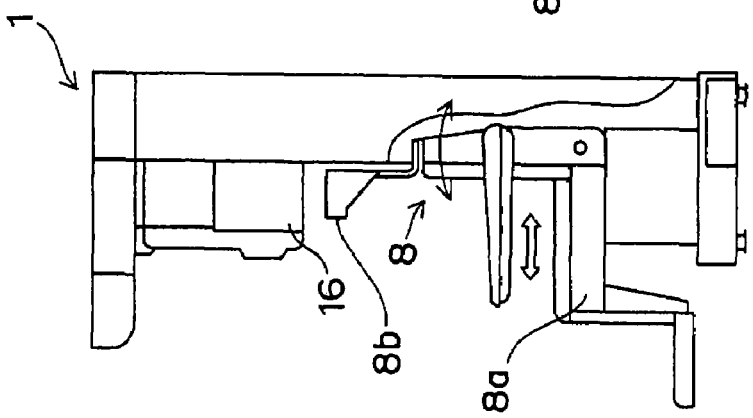
Figure 9C:
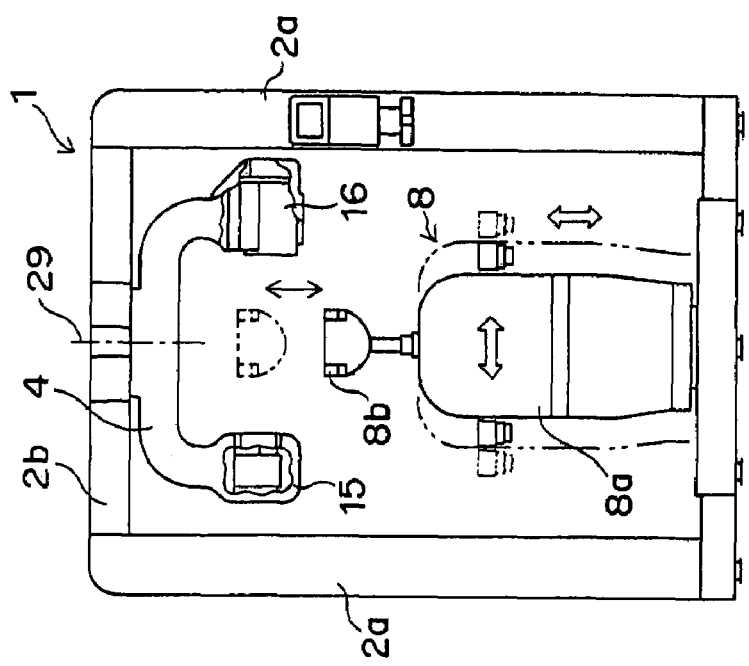

Further, as shown in FIG. 9, in a second example according to the present invention, the rotational arm 4 is supported by columns 2*a*, 2*a* having high rigidity and an upper frame 2*b*. The rotational arm 4 is uniaxially rotated, and the rotational central axis 29 is fixed. An region of interest is positioned by the positioning mechanism 8 having the XY movement mechanism 18.

The XY movement mechanism 18 has the pair of Y-direction guide rails 19Y fixed to a seat 8*aa* of a chair 8*a* and extending in the Y-direction, the Y-direction moving frame 20Y capable of reciprocating in the Y-direction along those Y-direction guide rails 19Y, the pair of X-direction guide rails 19X fixed to a base 8*ab* of the chair 8*a* and extending in the X-direction, and the X-direction moving frame 20X capable of reciprocating in the X-direction along those X-direction guide rails 19X. The Y-direction moving frame 20Y is coupled to the Y-direction moving motor 23Y fixed to the chair 8*a* through an appropriate drive transmission mechanism (e.g., mechanism including the screw 24Y drivingly coupled to the motor 23Y and the nut 25Y engaged therein and fixed to frame 20Y), so that the Y-direction moving frame 20Y moves in the Y-direction on the basis of drive of the Y-direction moving motor 23Y. Similarly, the X-direction moving frame 20X is coupled to the X-direction moving motor 23X fixed to the chair 8*a* through an appropriate drive transmission mechanism (e.g., mechanism including the screw 24X drivingly coupled to the motor 23X and the nut 25X engaged therein and fixed to the X-direction moving frame 20X), so that the X-direction moving frame 20X moves in the X-direction on the basis of drive of the X-direction moving motor 23X. As thus described, in the XY movement mechanism 18, the pair of Y-direction guide rails 19Y, the Y-direction moving frame 20Y, the Y-direction moving motor 23Y, and the drive transmission mechanism therefor (screw 24Y, nut 25Y) constitute the Y-direction movement mechanism, and the pair of X-direction guide rails 19X, the X-direction moving frame 20X, the X-direction moving motor 23X, and the drive transmission mechanism therefor (screw 24X, nut 25X) constitute the X-direction movement mechanism. Therefore, driving the moving motors 23X and 23Y can lead to arbitrary movement of the rotational central axis of the central axis.

It is to be noted that in the second example, the height (Z-direction) can also be adjusted by the chair 8*a*. Similarly to the X-direction movement mechanism and the Y-direction movement mechanism, a Z-direction movement mechanism is made up of a Z-direction moving motor 23Z and its drive transmission mechanism (nut 24Z, the nut 25Z), and capable of arbitrarily moving the height of the region of interest of the imaging object.

Further, the first example and the second example may be combined so as to provide respective XY movement mechanisms on the sides adjacent the rotational arm 4 and the chair 8*a*.

Figure 10:
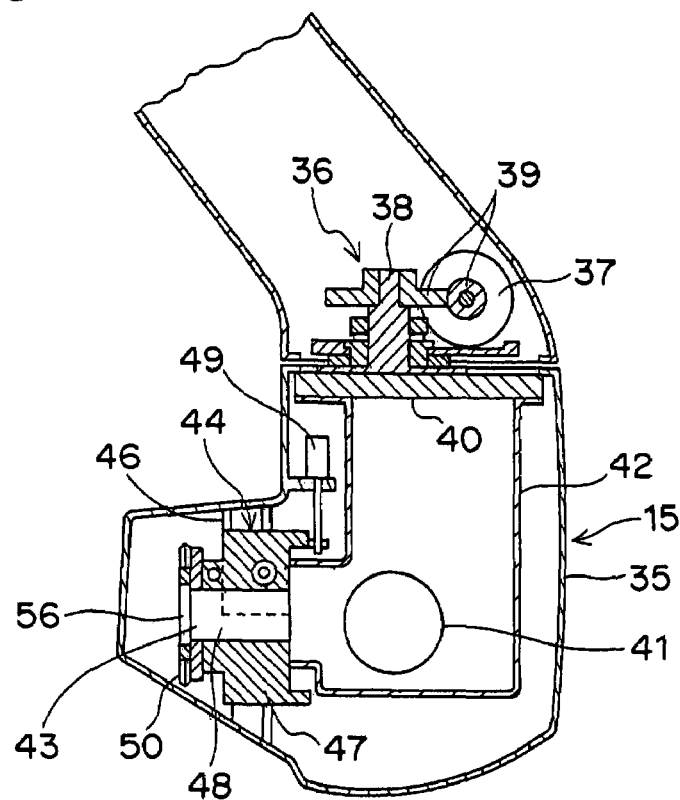
FIG. 10 is a sectional view of an X-ray generating section.

As shown in FIG. 10, the X-ray generating section 15 has an X-ray generating section housing 35 having various sorts of configurations described below. The X-ray generating section housing 35 is coupled to the rotational arm housing 17 through the X-ray generating section rotating mechanism 36. Specifically, in the X-ray imaging apparatus of the embodiment, an X-ray generating section rotating mechanism 36 has an X-ray generating section rotating motor 37 fixed to the inside of the rotational arm housing 17, a vertical axis 38 rotatably attached to the rotational arm housing 17, a gear mechanism 39 drivingly coupling the X-ray generating section rotating motor 37 and the vertical axis 38, and a fixed member 40 fixed to the X-ray generating section housing 35 and the vertical axis 38, such that the X-ray generating section housing 35 rotates with the vertical axis 38 as the center on the basis of drive of the X-ray generating section rotating motor 37. The X-ray generating section housing 35 is horizontally rotated for turning the X-ray generating section toward a head fixing apparatus for cephalometric imaging, not shown, in cephalometric imaging.

Figure 11:
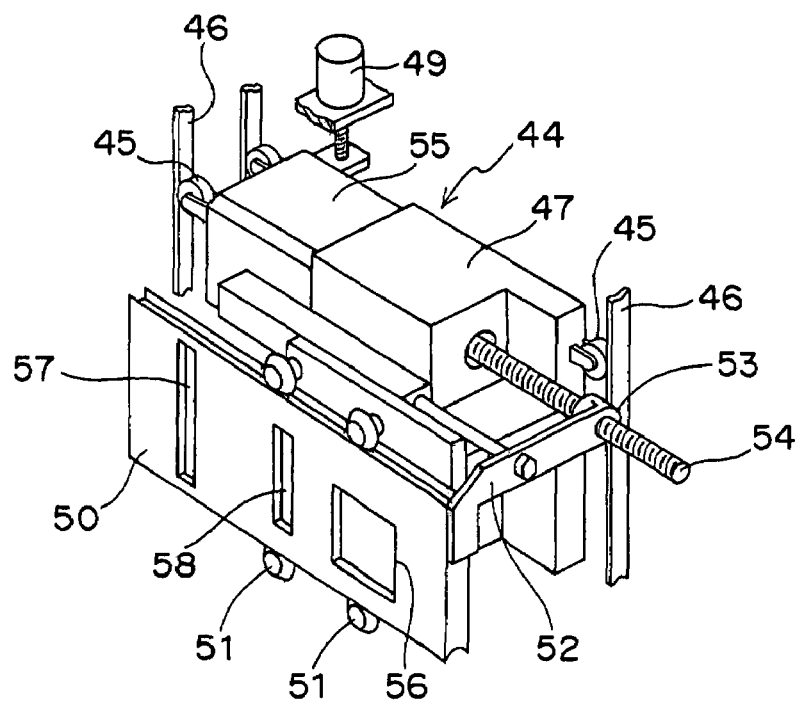
FIG. 11 is a perspective view showing a beam formation plate and the like which are built in the X-ray generating section.

An X-ray tube (X-rays generator) 41 as an X-ray generating source is housed inside the X-ray generating section housing 35. The X-ray tube 41 is surrounded by an X-ray blocking case 42 except for a region (region on the left side of FIG. 9) opposed to the X-ray detecting section 16. The X-ray blocking case 42 has a beam formation plate 50 in the region opposed to the X-ray detecting section 16, and a beam forming mechanism 44 is arranged on this beam formation plate 50. As shown in FIG. 11, the beam forming mechanism 44 has a support frame or a block 47 which is liftably supported along a plurality of vertical guide rails 46 through the plurality of guide rollers 45. The block 47 has an X-ray passage aperture 48 (see FIG. 10) which guides X-rays radiated from the X-ray tube 41 toward the X-ray detecting section 16, and is coupled to a block lifting motor 49 fixed to the X-ray generating section housing 35 through, for example, a spring mechanism, to allow up and down movement of an irradiation angle of X-rays on the basis of drive of the block lifting motor 49 so that a variety of angles and places can be imaged. It is thereby possible to move the irradiation angle of the X-rays up and down without up and down movement of the X-ray generating section 15.

Figure 13:
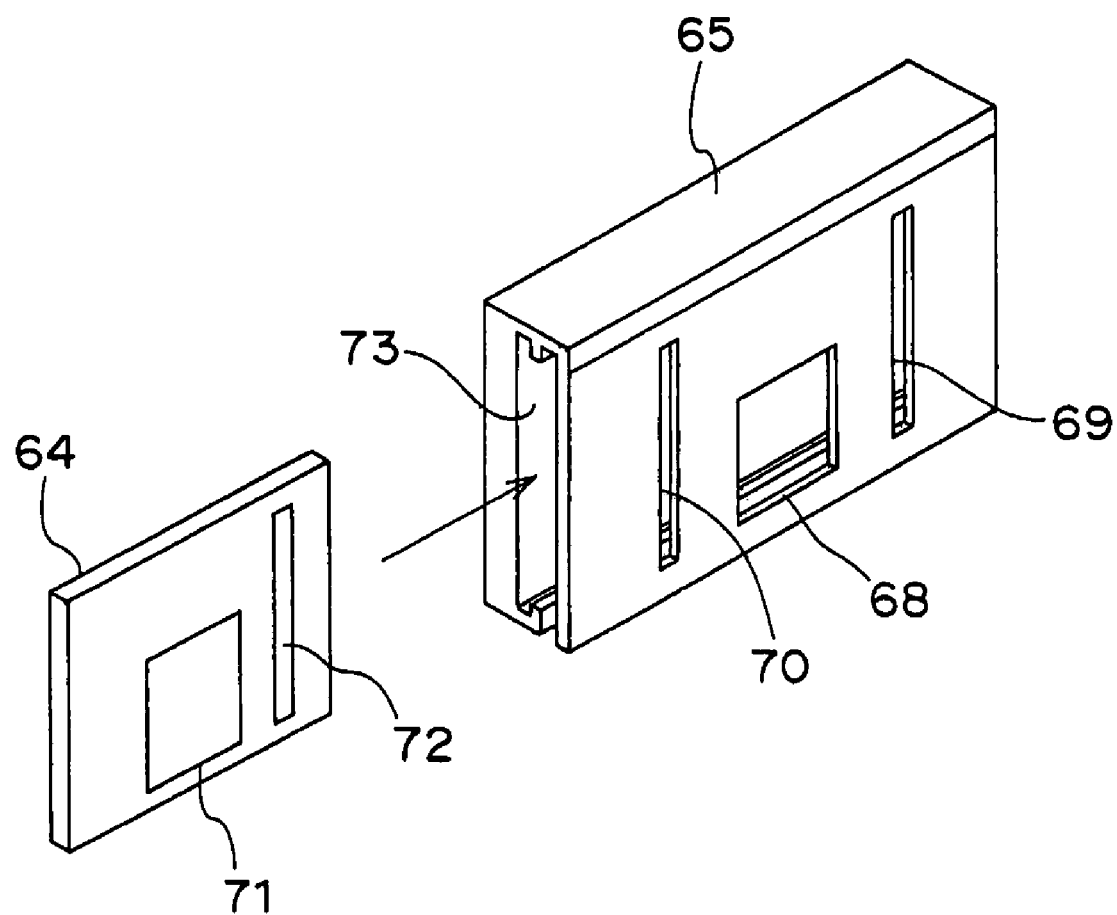
FIG. 13 is a perspective view of an X-ray detector.

At this time, imaging can be performed by enlarging an X-ray detecting device 71 shown in FIG. 13. Further, though not shown, with the use of a mechanism of moving the X-ray detecting device 71 up and down inside the X-ray detector 64, imaging can be performed even with a small X-ray detecting device.

A beam formation plate 50, having a plurality of beam formation slits as beam forming means of forming an X-ray beam radiated from the X-ray tube 41, is arranged in front of the block 47 and in particular, the outside of the X-ray passage aperture 48. The beam formation plate 50 is supported by a slit moving means which is horizontally movable by a plurality of guiding roller 51 fixed to the front face of the block 47. The slit moving means has a coupling arm 52 coupled to a beam formation plate 50, a nut 53 fixed to the coupling arm 52 is engaged in a horizontal screw axis 54 rotatably supported by the block 47, and further, the horizontal screw axis 54 is coupled to a beam formation plate moving motor 55 fixed to the block 47. Therefore, the beam formation plate 50 is capable of moving the front of the block 47 right and left, so as to apply a desired X-ray beam.

In the embodiment, the beam formation plate 50 has three beam forming slits (slit for primary formation). Specifically, these three beam forming slits include a beam forming transmission aperture 56 (first slit) for CT in a rectangular or a square shape (e.g. 120 mm in length and 120 mm in breadth), a beam forming transmission aperture 57 (second slit) for panoramic imaging which is vertically oriented (e.g. 150 mm in length and 6 mm in breadth), and a beam forming transmission aperture 58 for cephalometric imaging which is also vertically oriented. (e.g. 22 mm in length and 6 mm in breadth). Therefore, in a state where the beam forming transmission aperture 56 for CT is opposed to the X-ray tube 41 through the X-ray passage aperture 48, an X-ray cone beam extending in a pyramid shape is radiated from the X-ray generating section 15 toward the X-ray detecting section 16. In the case of using such a cone beam for CT, it is possible to perform CT for example in a range with a diameter of the order of 60 mm and a height of the order of 60 mm as an imaging region.

In the embodiment, since the length and breadth of the beam forming transmission aperture 56 for CT are the same, the cross section of the X-ray beam which is orthogonal to a traveling direction has a square shape. In a state where the beam forming transmission aperture 57 for panoramic imaging or the beam forming transmission aperture 58 for cephalometric imaging is opposed to the X-ray tube 41 through the X-ray passage aperture 48, an X-ray narrow beam is radiated from the X-ray generating section 15 toward the X-ray detecting section 16 in a long flat plate shape having a cross section with its longitudinal length larger than its lateral length, though strictly in the pyramid shape.

Figure 12:
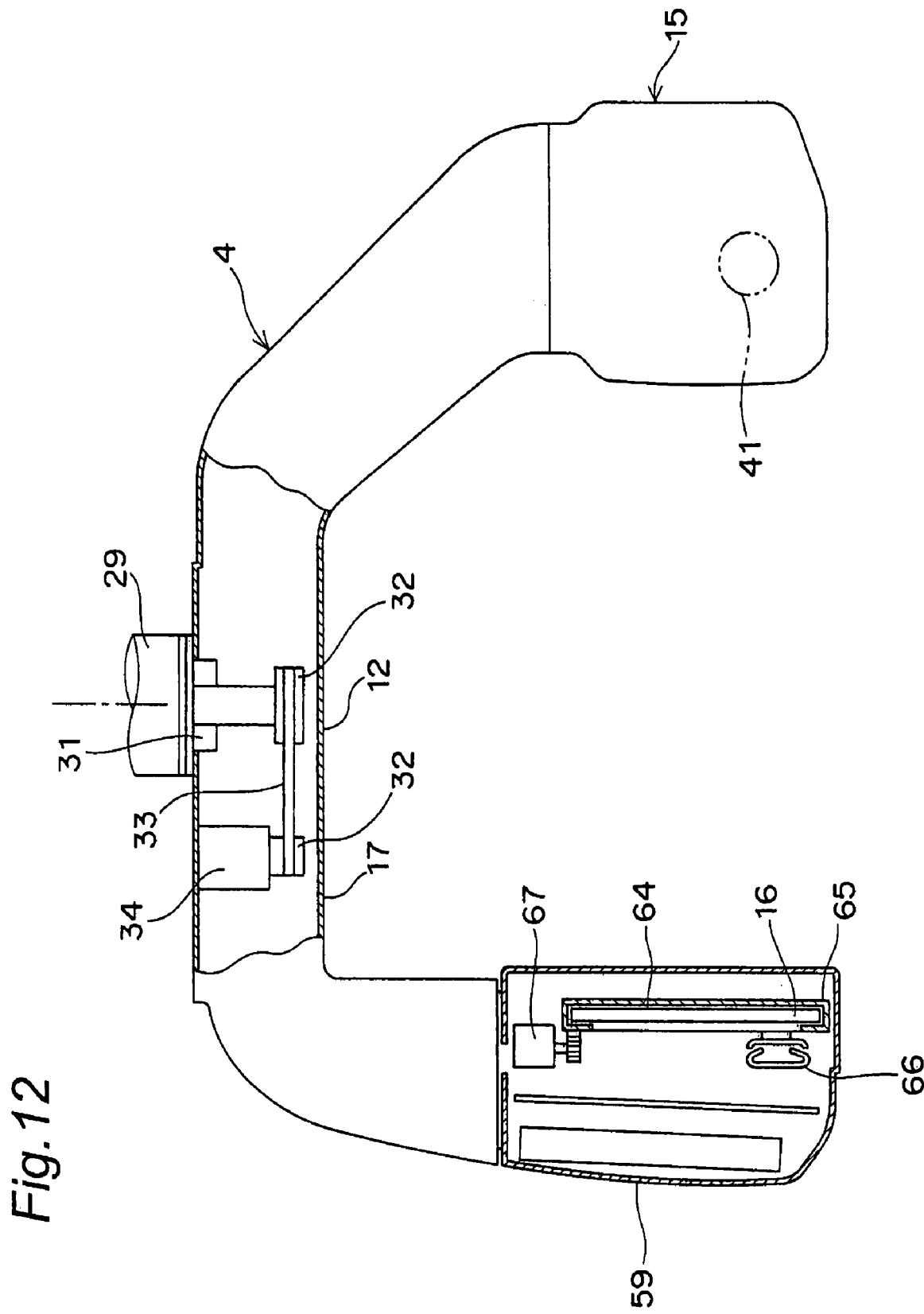
FIG. 12 is a front view of a part cut out from the rotational arm has been cut out.

As shown in FIG. 12, the X-ray detecting section 16 has an X-ray detecting section housing 59 surrounding a variety of configurations which are described below.

In the inside of the X-ray detecting section housing 59, a detector holder 65 is provided for housing an X-ray detector (X-ray detecting section) 64 having a solid-state image sensing device (CCD) configured by arranging semiconductor image pickup devices in the longitudinal and lateral directions. The detector holder 65 is movably supported in the horizontal direction along a holder guide rail 66 and coupled to the X-ray detecting section moving motor 67 fixed to the X-ray detecting section housing 59, so as to move in the horizontal direction on the basis of drive of the X-ray detecting section moving motor 67. The CCD is not necessarily applied to the X-ray detecting section, but a flat panel detector (FPD) such as a MOS sensor, and an X-ray fluorescent multiplier tube (XII) may be applied.

As shown in FIG. 13, the detector holder 65 has a plurality of beam formation slits (slit for secondary formation) 68, 69, 70 in shapes corresponding to the forgoing plurality of beam forming transmission apertures 56, 57, 58 in the X-ray generating section 15, and on the basis of drive of the X-ray detecting section moving motor 67 according to the imaging mode, the beam formation slit 68, 69 or 70 in the X-ray detecting section 16 which correspond to the beam forming transmission aperture in the X-ray generating section 15 is positioned in extension of the X-ray tube 41 and the beam forming transmission apertures 56, 57 or 58 in the X-ray generating section 15 in accordance with a selection signal of the imaging mode selecting means. The X-ray detector 64 has: an X-ray detecting device 71 obtained by arranging image pickup devices in almost square shape corresponding to the beam formation slit 68 in almost square shape; and an X-ray detecting device 72 obtained by arranging image pickup devices in a shape vertically oriented corresponding to the vertically oriented beam formation slits 69 and 70. The X-ray detector 64 is inserted into a slot 73 formed in the detector holder 65. The X-ray detecting device 71 is arranged behind the beam formation slit 68 in X-ray CT, and the X-ray detecting device 72 is arranged behind the beam formation slits 69 and 70 in panoramic imaging or in cephalometric imaging.

Figure 14:
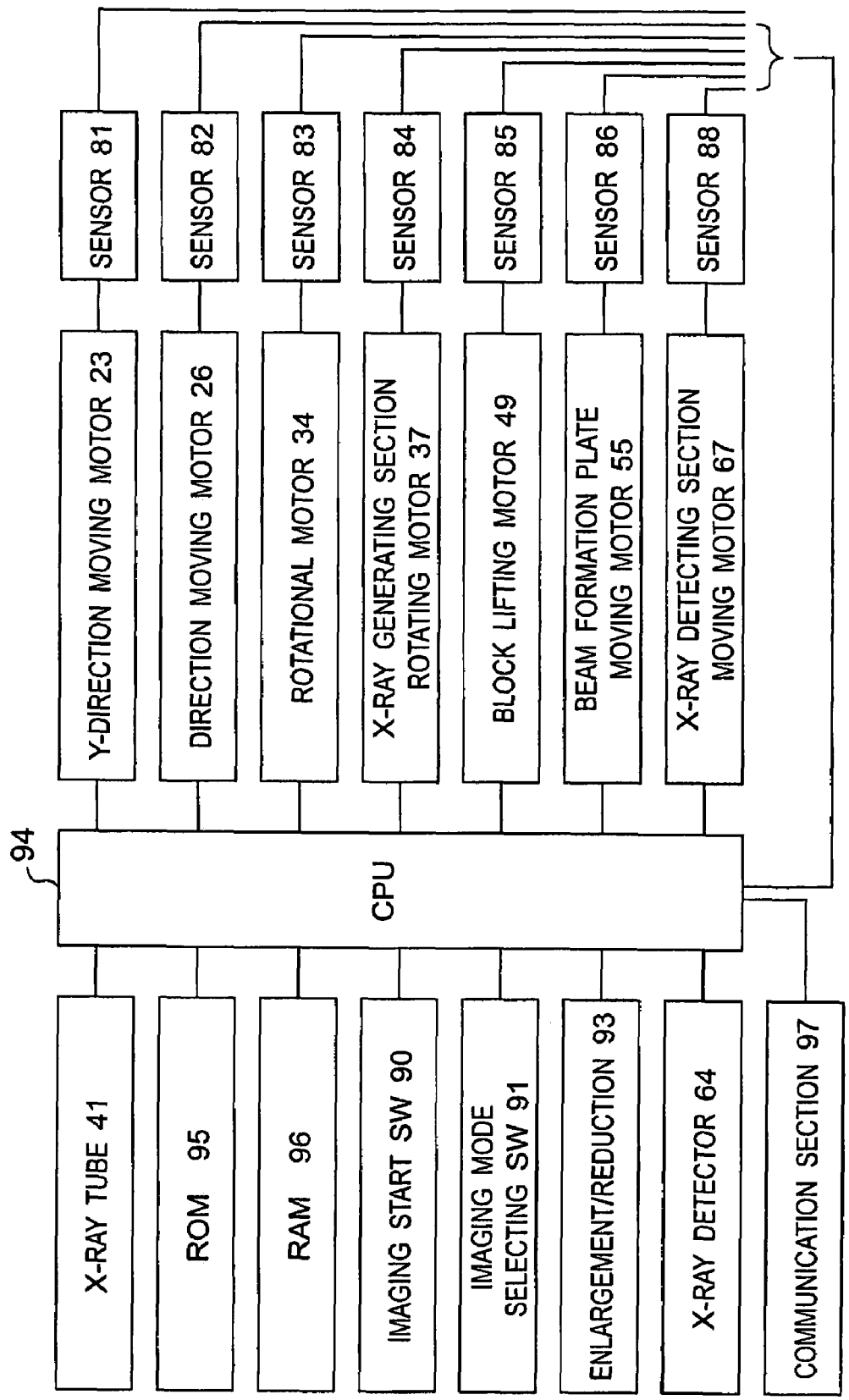
FIG. 14 is a control block diagram for the X-ray imaging apparatus.

FIG. 14 is a control block diagram of a plurality of motors and the like included in the X-ray CT apparatus 1. As shown in the figure, the X-ray imaging apparatus has a controller (CPU) 94. The CPU 94 is connected with the foregoing plurality of motors, namely, the Y-direction moving motor, the X-direction moving motor 26, the rotational motor 34, the X-ray generating section rotating motor 37, the block lifting motor 49, the beam formation plate moving motor 55, and the X-ray detecting section moving motor 67. These motors are connected to corresponding rotational amount detecting sensors (e.g. encoder) 81 to 88 for the purpose of detecting rotational amounts thereof and controlling drive of the motors on the basis of the detected rotational amounts, and outputs of these sensors 81 to 88 are connected to the CPU 94.

The CPU 94 is also connected with the X-ray tube 41 and a plurality of storage sections. The storage sections have movement locus data (Read Only Memory: ROM) 95, and an X-ray image storing section (Random Access Memory: RAM) 96. The ROM 95 stores the following information during imaging (including processes before and after imaging) in accordance with each image mode described later, a movement amount in an XY direction of the rotational central axis 29, rotation of the rotational central axis 29 (rotational angle of the rotational arm 4), rotational angles of the X-ray generating section housing 35 and the X-ray detecting section housing 59 against the rotational arm 4, a moving amount in the up-and-down direction and the horizontal direction of the block 47 and a movement amount in the horizontal direction of the beam formation plate 50 in the X-ray generating section 15, and movement amounts in the horizontal direction of the X-ray detector 64 and the detector holder 65 in the X-ray detecting section 16. In particular, the movement amount of the rotational central axis 29 and the movement amount of the rotational arm 4 are defined by data with parameters being time and a coordinate value of an XY coordinate system made up of axes in two orthogonal directions (e.g., a back and forth direction in which the upper and lower arm sections 6 and 7 project in the lifting arm 3 and a horizontal direction orthogonal thereto) on the horizontal plane. The coordinate value may be given by a polar coordinate instead of the XY coordinate system.

The RAM 96 temporarily stores necessary information. For example, as shown in the figure, the X-ray detector 64 is electrically connected to the CPU 94 while being in the state of being mounted on the X-ray detecting section 16, and image data acquired in the X-ray detector 64 by X-ray imaging is temporarily stored into the RAM 96.

The CPU 94 is further connected with an imaging start switch 90 for starting X-ray imaging, an imaging mode selecting switch 91 for switching an imaging mode, such as the normal scan/CT mode, the offset scan/CT mode, the panoramic X-ray imaging mode, and the cephalometric imaging mode, a changing-over switch 93 for making switching between a reduced (wide area) imaging mode in which a wide area of an imaging object is imaged and an enlarged (narrow) imaging mode in which a narrow area of the imaging object is enlarged and imaged, and a communication section 97 for performing communication with a computer, not shown.

Figure 15:
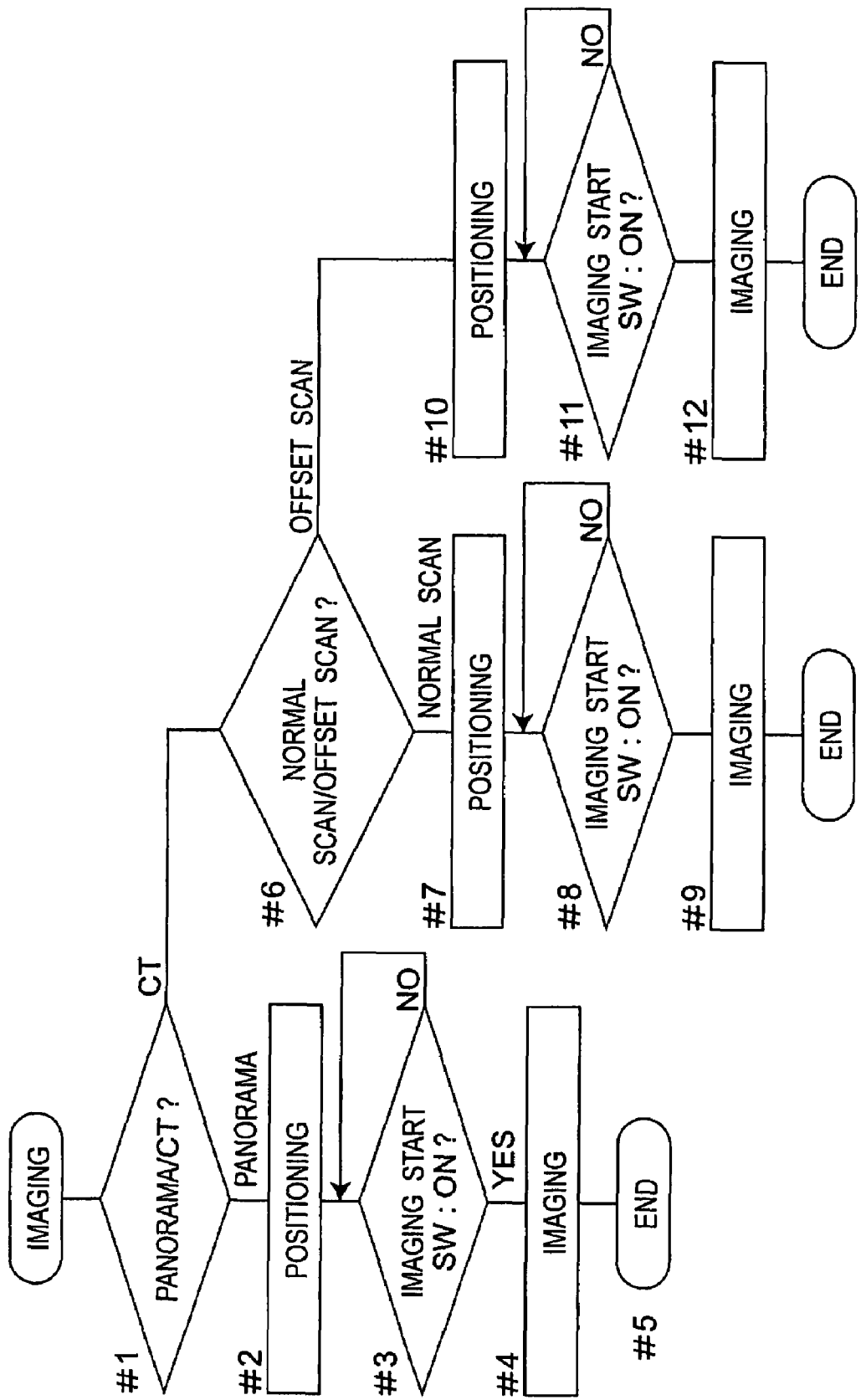
FIG. 15 is a flowchart showing a control program for the X-ray imaging apparatus.

A basic operation of the X-ray imaging apparatus having such a configuration is described with reference to the block diagram of FIG. 14 and a flowchart of FIG. 15. First, as shown in FIGS. 5 and 9, the imaging object is positioned in the X-ray CT apparatus 1 by the positioning mechanism 8 prior to imaging. At this time, in the first example shown in FIG. 5, the imaging object stands in front of the lower arm section 7 of the lifting arm 3, holds the handles 11 with his or her both hands, and puts his or her jaw on the chin rest 9 while a right-and-left movement of his or her head is in the state of being restricted by the right and left lateral direction control member 10. Further, in the second example shown in FIG. 9, the imaging object sits on the chair 8a while his or her head is in the state of being restricted so as to remain still by a head fixing apparatus 8b.

An operator operates the imaging mode selecting switch 91 to select an imaging mode (panoramic imaging, CT or the like). Further, when the CT mode has been selected, a normal scan/CT-offset scan/CT mode selecting switch 92 is operated to select either the normal scan/CT mode or the offset scan/CT mode. It is to be noted that the normal scan/CT mode is a mode in which the rotational arm 4 is rotated with the rotational central axis 29 as the center, and X-rays having been radiated from the X-ray generating section 15 and transmitted through the whole of the region of interest 105 of the imaging object are detected in the X-ray detecting section 16, and on the basis of information included in the X-rays having transmitted through the whole of the region of interest 105 of the imaging object and been detected in the X-ray detecting section 16, a tomographic image of an imaging object arranged between the X-ray generating section 15 and the X-ray detecting section 16 is constructed. Further, the offset scan/CT mode is a mode in which the rotational arm 4 is rotated with the rotational central axis 29 as the center, and X-rays having been radiated from the X-ray generating section 15 and transmitted through part of the region of interest 105 of the imaging object are detected in the X-ray detecting section 16, and on the basis of information included in the X-rays having transmitted through the part of the region of interest 105 of the imaging object and been detected in the X-ray detecting section 16, a tomographic image of the imaging object arranged between the X-ray generating section 15 and the X-ray detecting section 16 is constructed. In the present embodiment, in the normal scan/CT mode, a CT image of the imaging object is constructed on the basis of X-ray imaging data obtained by arranging a center 100 of the region of interest 105 of the imaging object which radiated from the X-ray generating section 15 and detected in the X-ray detecting section 16 on the same axis as the rotational central axis 29 and rotating the center.

In the normal scan/CT mode, since imaging is performed while the region of interest 105 is constantly present in a cone beam 104 irrespective of the rotational angle of the rotational arm 4, an image can be reconstructed on the basis of X-ray transmission information obtained during rotation of the rotational arm of 180 degrees. Further, the rotational arm is more favorably rotated 360 degrees for reconstitution of a fine image. Imaging can be performed in a wide area in the offset scan/CT mode as compared with the normal scan/CT mode.

Moreover, according to the offset scan/CT mode, for example when an FPD with a size of 120 mm×120 mm of the present example is used, imaging can be performed in a range with a diameter of the order of 120 mm and a height of the order of 60 mm, whereas in the normal scan/CT mode, imaging can be performed only in a range with a diameter of the order of 60 mm and a height of the order of 60 mm.

When the panoramic imaging mode has been selected, the CPU 94 reads a program (not shown) in accordance with the panoramic imaging mode from the ROM 95, and drives, if necessary, one or more than one of the Y-direction moving motor 23Y, the X-direction moving motor 23X and the rotational motor 34 simultaneously or sequentially on the basis of the read program, to move the rotational arm 4, the X-ray generating section 15 and the X-ray detecting section 16 to initial imaging positions (Step #2). Further, the CPU 94 drives the beam formation plate moving motor 55, to make the beam forming transmission aperture 57 for panoramic imaging in accordance with the selected panoramic imaging mode opposed to the X-ray tube 41.

After completion of the above-mentioned preparation, when a command to start panoramic imaging is inputted by operation of the imaging start switch 90 (Step #3), the CPU 94 drives the Y-direction moving motor 23Y, the X-direction moving motor 23X, the rotational motor 34 and the like on the basis of a program read from the ROM 95, and also activates the X-ray tube 41 to generate X-rays (Step #5). As a result, while the rotational arm 4, the X-ray generating section 15 and the X-ray detecting section 16 move along loci indicated by the program, the X-rays radiated from the X-ray tube 41 are applied to the imaging object through the X-ray passage aperture 48 of the block 47 and the beam forming transmission aperture 57 for panoramic imaging of the beam formation plate 50. The X-rays having transmitted through the imaging object are detected by the X-ray detector 64 through the beam formation slit for panoramic imaging of the X-ray detector 64 in the X-ray detecting section 16. The X-ray detecting section 16 transmits data corresponding to the detected X-ray image to the RAM 96 at regular time intervals or after completion of imaging. The image data stored in the RAM 96 is transmitted to a computer through the communication section 97, and objected to a necessary process therein, to be displayed on a display, not shown. A typical imaging process in panoramic X-ray imaging is a known process, namely an imaging process of laminating frame images with displacement of a prescribed amount. Further, panoramic X-ray imaging can be performed prior to CT, to set an region of interest to be objected to CT.

When the CT mode has been selected by the imaging mode selecting switch 91, the CPU 94 determines either the normal scan/CT mode (first imaging mode) or the offset scan/CT mode (second imaging mode) has been selected on the basis of a signal from the normal scan/CT-offset scan/CT mode selecting switch 93 (Step #6).

When the normal scan/CT mode has been selected, the CPU 94 drives the beam formation plate moving motor 55 to make the beam forming transmission aperture 56 for CT in accordance with the selected CT mode opposed to the X-ray tube 41. Next, the CPU 94 reads a program (not shown) in accordance with the selected normal scan/CT mode from the ROM 95, and drives, if necessary, one or more than one of the Y-direction moving motor 23Y, the X-direction moving motor 23X and the rotational motor 34 simultaneously or sequentially on the basis of the read program, to move the rotational arm 4 to the initial imaging position (Step #7). Typically, in this state, the center of the driving axis 30 is placed on a line linking the X-ray generating section 15 (center of the X-ray tube 41) and the X-ray detecting section 16 (center of the X-ray detecting device 71).

Subsequently, when a command to start imaging is inputted by operation of the imaging start switch 90 (Step #8), the CPU 94 activates the X-ray tube 41 to generate X-rays, also drives a necessary motor in accordance with the foregoing program (Step #9). At this time, the rotational amount of each motor is detected by the corresponding sensors 81 to 88, and using this detection result, the rotational amount of each motor is feedback-controlled. The X-rays radiated from the X-ray tube 41 are applied to the imaging object through the X-ray passage aperture 48 of the block 47 and the beam forming transmission aperture 56 for CT of the beam formation plate 50. The X-rays having transmitted through the imaging object are detected by the X-ray detector 64 through the beam formation slit for panoramic imaging of the X-ray detector 64 in the X-ray detecting section 16. The X-ray detecting section 16 stores data corresponding to the detected X-ray image into the RAM 96 at regular time intervals. The image data stored in the RAM 96 is transmitted to the computer through the communication section 97, and objected to a necessary process therein, to be displayed on the display, not shown. At this time, a necessary image is reconstructed through the use of image data obtained by detecting X-rays having transmitted through both side regions sandwiching the rotational central axis 29.

When the offset scan/CT mode has been selected, the CPU 94 drives the beam formation plate moving motor 55 to make the beam forming transmission aperture 56 for CT in accordance with the selected CT mode opposed to the X-ray tube 41. At this time, if necessary, the block 47 is moved in a rotational direction relatively to the beam formation plate 50 in the X-ray generating section 15, and meanwhile, the detector holder 65 is moved in the rotational direction in the X-ray detecting section 16. Further, the CPU 94 reads a program (not shown) in accordance with the selected offset scan/CT mode from the ROM 95, and drives, if necessary, one or more than one of the Y-direction moving motor 23Y, the X-direction moving motor 23X and the rotational motor 34 simultaneously or sequentially on the basis of the read program, to move the rotational arm 4 to the initial imaging position (Step #10).

Subsequently, when a command to start imaging is inputted by operation of the imaging start switch 90 (Step #11), the CPU 94 activates the X-ray tube 41 to generate the X-ray tube 41, and also drives a necessary motor in accordance with the foregoing program (Step #12). At this time, the rotational amount of each motor is detected by the corresponding sensors 81 to 88, and on the basis of this detection result, the rotational amount of each motor is feedback-controlled. The X-rays radiated from the X-ray tube 41 are applied to the imaging object through the X-ray passage aperture 48 of the block 47 and the beam forming transmission aperture 56 for CT of the beam formation plate 50. The X-rays having transmitted through the imaging object are detected by the X-ray detector 64 through the beam formation slit for CT of the X-ray detector 64 in the X-ray detecting section 16. The X-ray detecting section 16 stores data corresponding to the detected X-ray image to the RAM 96 at regular time intervals. The image data stored in the RAM 96 is transmitted to the computer through the communication section 97, and objected to a necessary process therein, to be displayed on the display, not shown. At this time, a necessary image is reconstructed through the use of image data obtained by detecting X-rays having transmitted through one of both side regions sandwiching the rotational central axis 29.

An initial setting process in the case where the offset scan/CT mode has been selected is described with reference to FIG. 15. It is assumed here that in the state prior to the initial setting process, the rotational central axis 29 of the X-ray CT apparatus 1 is located at a center 100 of an imaging region 101 (region surrounded by an outer circle out of double circles) of the imaging object which is positioned by the positioning mechanism 8 of the imaging object. As shown in the figure, in this state, the imaging region 101 of the imaging object is not completely included in an X-ray irradiating region (region surrounded by outer edges 102 and 103 indicated by the two dotted lines) 104 detected in the X-ray detecting section 16 out of X-rays radiated from the X-ray generating section 15, and only an region of interest (region surrounded by an inner circle out of the double circles) 105 inside the imaging region 101 of the imaging object can be imaged.

Figure 16:
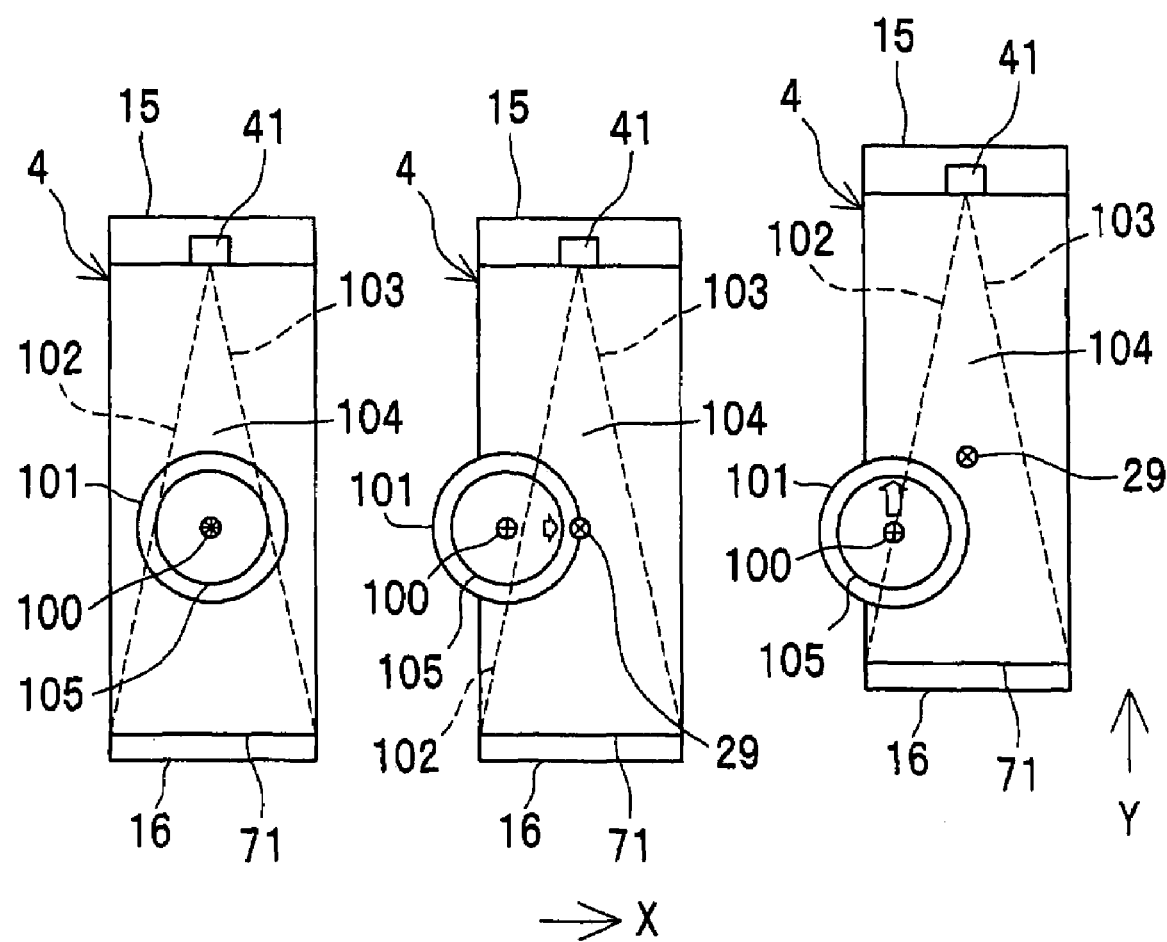
FIG. 16 is a pattern view explaining an initial setting process for a reduced CT mode.

From this state, with the position of the imaging object in a fixed state, the CPU 94 drives the X-direction moving motor 23X of the XY movement mechanism 18 to move the rotational arm 4 in the X-direction (direction to the right, direction of the arrow in the shown example) by a prescribed distance from the position of FIG. 16A, while locating the rotational central axis 29 at the center of the imaging region 101 of the imaging object from the position of FIG. 16A (see FIG. 16B). Subsequently, while keeping the rotational central axis 29 located at the center of the imaging region 101 of the imaging object, the CPU 94 moves the rotational arm 4 in the Y-direction (direction upward, direction of the arrow in the shown example) to bring the X-ray detecting section 16 closer to the imaging region 101 of the imaging object so as to locate the outer edge 102 or 103 of the cone beam 104 at the center of the imaging region 101 (see FIG. 16C). At this time, the outer edge 102 or 103 of the cone beam 104 is not necessarily at the center of the imaging region 101 of the imaging object, but at least the center of the imaging region 101 needs to be located inside the cone beam 104. As shown in the figure, in this state, half of the imaging region 101 of the imaging object is completely included in the cone beam 104.

Figure 17:
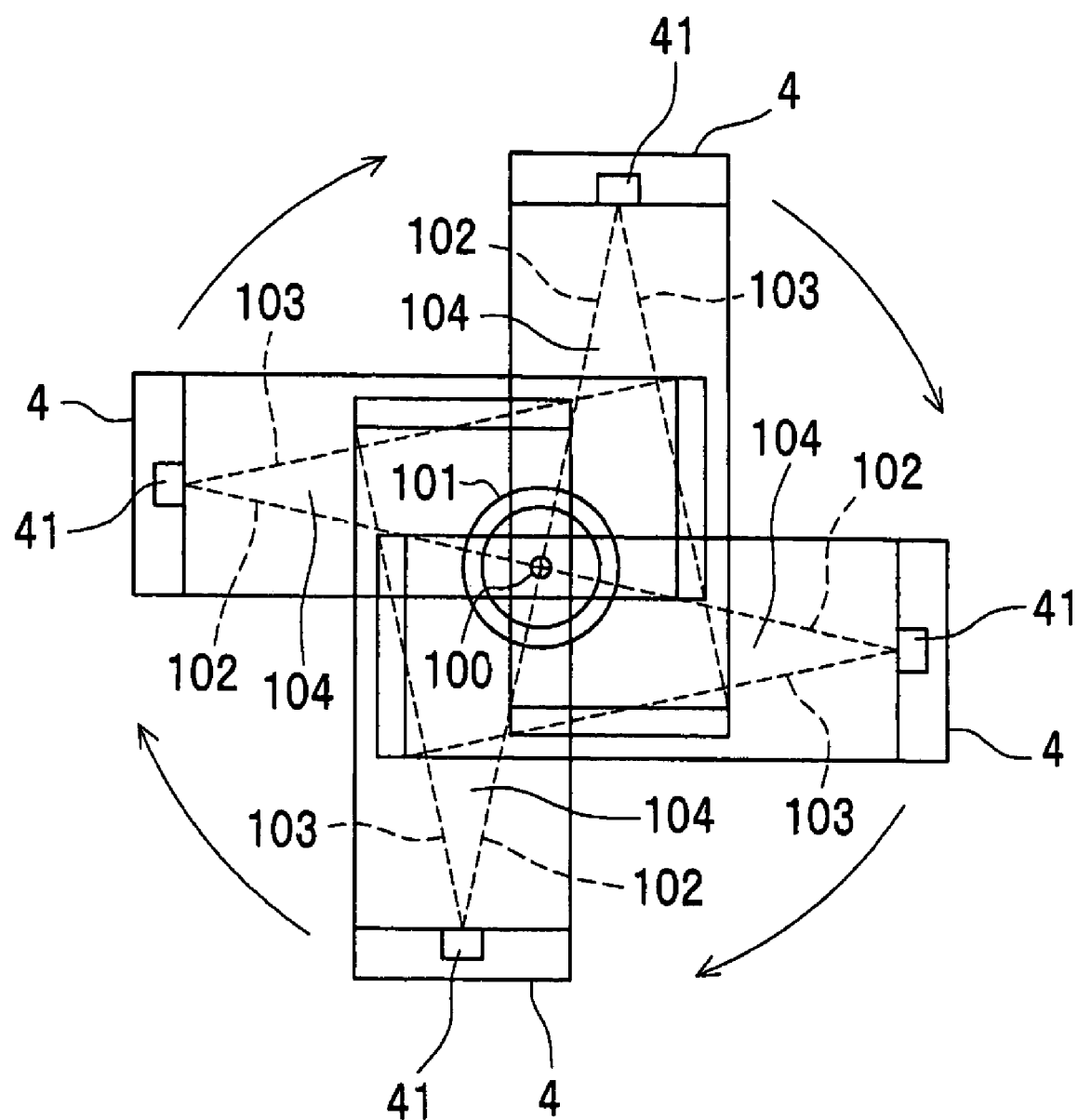
FIG. 17 is a pattern view showing an operation of the rotational arm in the reduced CT mode.

Subsequently, as shown in FIG. 17, the CPU 94 drives the rotational motor 34 to rotate the rotational arm 4 in a clockwise direction as indicated by the arrows. As a result, although the cone beam 104 covers only half of the imaging region 101 of the imaging object at each time point during imaging, when the rotational arm 4 rotates completely (360 degrees), the imaging region 101 of the imaging object is entirely scanned by the cone beam 104. This can result in subsequent reconstruction of X-ray imaged image data detected in the X-ray detecting section 16, thereby allowing reconstruction of a desired image of the entire imaging region 101 of the imaging object. Such imaging is called offset scan/CT, which can be performed in a wider range than the normal scan/CT.

The initial setting process in a case where the enlarged (narrow) mode has been selected is described with reference to FIG. 18. Similarly to what was described above, it is assumed that in the state prior to the initial setting process, the rotational central axis 29 of the X-ray CT apparatus 1 is located at the center of the imaging region 101 (region surrounded by an outer circle out of double circles) of the imaging object which is positioned by the positioning mechanism 8 of the imaging object. As shown in the figure, in this state, the imaging region 101 of the imaging object is not completely included in the X-ray irradiating region (region surrounded by the outer edges 102 and 103 indicated by the two dotted lines) 104 detected in the X-ray detecting section 16 out of X-rays radiated from the X-ray generating section 15, and only the region of interest (region surrounded by an inner circle out of the double circles) 105 inside the imaging region 101 of the imaging object can be imaged.

From this state, the CPU 94 drives the X-direction moving motor 23X of the XY movement mechanism 18 to move the rotational arm 4 in the X-direction (direction to the right, direction of the arrow in the shown example) by a prescribed distance, while locating the rotational central axis 29 at the center of the imaging region 101. Subsequently, while keeping the rotational central axis 100 located at the center of the imaging region 101 of the imaging object, the CPU 94 moves the rotational arm 4 in the Y-direction (direction downward, direction of the arrow in the shown example) to bring the imaging region 101 of the imaging object closer to the X-ray generating section 15 so as to locate the outer edge 102 or 103 of the cone beam 104 at the center of the imaging region 101. At this time, the outer edge 102 or 103 of the cone beam 104 is not necessarily at the center of the imaging region 101 of the imaging object, but at least the center of the imaging region 101 needs to be located inside the cone beam 104. As shown in the figure, in this state, half of the imaging region 101 of the imaging object is completely included in the cone beam 104.

Figure 19:
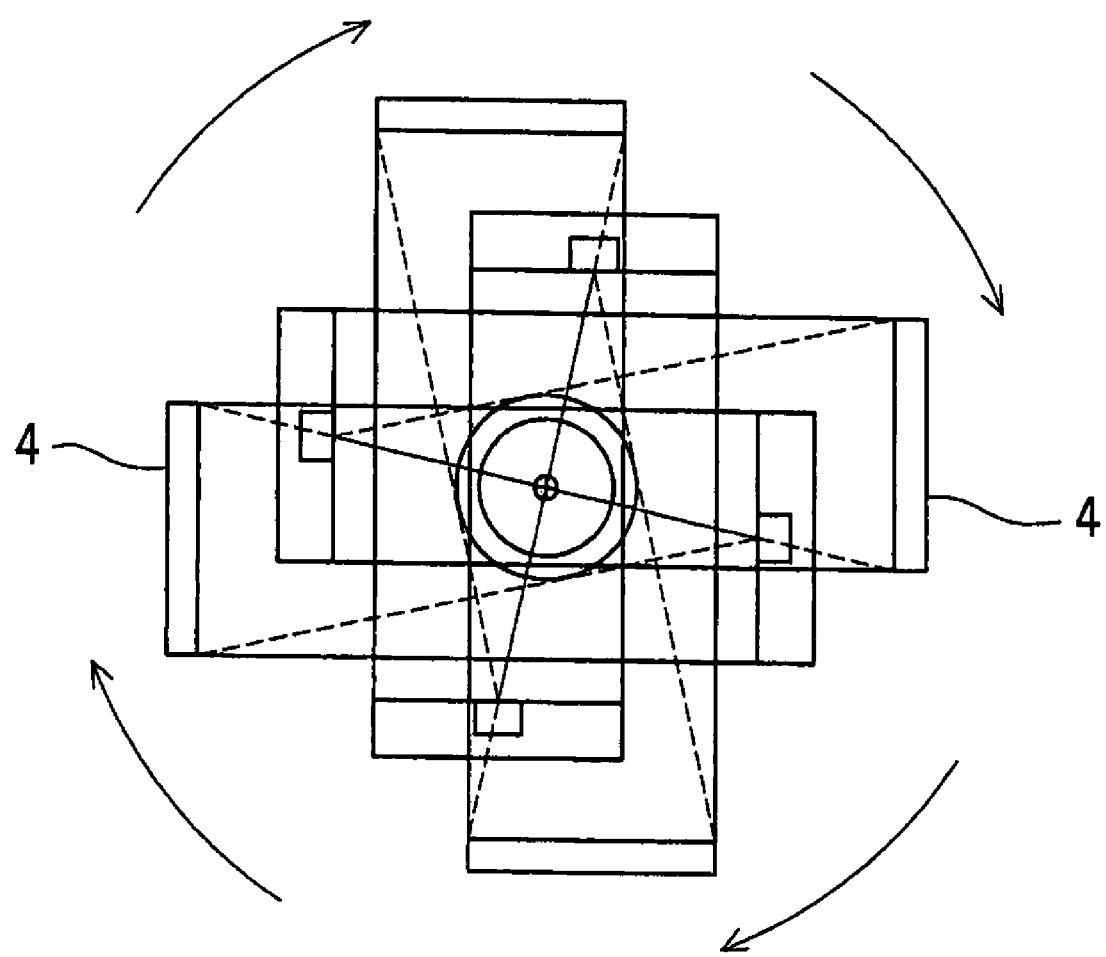
FIG. 19 is a pattern view showing an operation of the rotational arm in the enlarged CT mode.

Subsequently, as shown in FIG. 19, the CPU 94 drives the rotational motor 34 to rotate the rotational arm 4 in a clockwise direction as indicated by the arrows As a result, although the cone beam 104 covers only half of the imaging region 101 of the imaging object at each time point during imaging, when the rotational arm 4 rotates 360 degrees, the imaging region 101 of the imaging object is entirely scanned by the cone beam 104. This can result in subsequent reconstruction of X-ray imaged image data detected in the X-ray detecting section 16, thereby allowing reconstruction of a desired image of the entire imaging region 101 of the imaging object. By performing imaging in such a manner, a projected image can be enlarged and imaged since the distance between the X-ray source and the imaging object is shorter than in the case of FIG. 16.

In these preferred embodiments, An imaging region at normal scan/CT mode is defined as a region of interest as an example.

The imaging region at normal scan/CT mode is a region like the region of circle 105 in FIG. 16A or FIG. 18A.

And an imaging region at offset scan/CT mode is for example an region includes the imaging region at normal scan/CT mode and the region around the imaging region at normal scan/CT mode like the region of circle 101 in FIG. 16A or FIG. 18A.

Therefore the maximum region of the imaging region at offset scan/CT mode is defined by outer edges 102 or 103 of conebeam 104.

In FIG. 16A to C, FIG. 18A to C the imaging region 101 is indicated as an example smaller than the maximum region of the imaging region above mentioned considering the convenience for understanding.

It is to be noted that, although the rotational arm 4 was first moved in the X-direction and then moved in the Y-direction in the above description, this order may be reversed, or the rotational arm 4 may be moved all at once in an oblique direction obtained by synthesizing those movements in the two directions.

The X-direction movement mechanism provided in the rotational arm 4 is particularly effective in the X-ray imaging apparatus having the offset scan/CT mode, as described above. For example, the cone beam need to be moved to the direction orthogonal to the X-ray applying direction in the offset scan/CT method, but the movement amount thereof can be adjusted in a wider range. Further, an enlargement ratio of an image imaged in the X-ray detecting section of limited size can be adjusted in a large scale as compared with a constitution where the rotational arm is simply moved in the Y-direction.

In addition, the cone beam refers to an X-ray beam that narrows X-rays so as to apply X-rays within a certain region. In the above examples, the beam forming transmission aperture for CT was in almost square shape and the cone beam in the pyramid shape was applied from the X-ray generating section toward the X-ray detecting section. However, a shape of the beam forming transmission aperture for CT is not restricted to this, but a cone beam in cone shape can be formed when the beam forming transmission aperture is formed into circular or oval shape.

What is claimed is:

1. An X-ray CT apparatus, which comprises an X-ray generating section that applies X-rays and an X-ray detecting section in opposing positions, and which rotates said X-ray generating section and X-ray detecting section with an imaging object arranged between said X-ray generating section and X-ray detecting section and also detects X-rays having been radiated from said X-ray generating section and transmitted through said imaging object in said X-ray detecting section to back-project X-ray CT data, so as to form a CT image, wherein said apparatus comprises an imaging mode selecting device for selecting:

a panoramic imaging mode in which, during imaging, a rotational arm having said X-ray generating section and X-ray detecting section is rotationally driven while a rotational central axis of the rotational arm is moved, to form a panoramic image of said imaging object; and an offset scan/CT mode in which a CT image of said imaging object is constructed on the basis of X-ray CT data obtained by rotating the rotational arm around a rotational central axis wherein the rotational arm is set in such a position as a part of a region of interest of said imaging object is constantly irradiated with a cone beam radiated from said X-ray generating section and detected in said X-ray detecting section.

2. The X-ray CT apparatus according to claim 1, wherein said imaging mode selecting device has a normal scan/CT mode in which a CT image of said imaging object is constructed on the basis of X-ray CT data obtained by rotating the rotational central axis of the rotational arm as the center that is provided in such a position as to constantly irradiate a region of interest of said imaging object with a cone beam radiated from said X-ray generating section and detected in said X-ray detecting section.

3. The X-ray CT apparatus according to claim 2, wherein said X-ray generating section has:

a first slit which forms an X-ray beam, radiated from the X-ray generating section, into narrow strip shape to rotate a narrow beam toward said imaging object in accordance with said panoramic imaging mode;

a second slit which forms an X-ray beam, radiated from the X-ray generating section toward said imaging object, into a cone beam in accordance with at least either one of said offset scan/CT mode and said normal scan/CT mode; and a slit moving device for selectively arranging said first slit and said second slit in said X-ray generating section.

4. The X-ray CT apparatus according to claim 3, wherein said apparatus is provided with a device for moving the first slit or the second slit arranged in said X-ray generating section to a direction orthogonal to said X-ray beam in accordance with a signal from said imaging mode selecting device.

5. The X-ray CT apparatus according to any one of claims 2 to 4, comprising a driving device for moving the rotational central axis of the rotational arm against the rotational arm to set in such a position as to constantly irradiate a part or the whole of a region of interest of said imaging object with said cone beam in accordance with at least one of said offset scan/CT mode and said normal scan/CT mode.

6. The X-ray CT apparatus according to any one of claims 1 to 4, comprising a driving device for moving said rotational central axis in accordance with a rotational angle of the rotational arm that holds said X-ray generating section and said X-ray detecting section.

* * * * *